United States Patent
Matsufuji et al.

(10) Patent No.: US 11,523,976 B2
(45) Date of Patent: *Dec. 13, 2022

(54) COMPOSITE PIGMENT AND METHOD FOR PREPARING THE SAME

(75) Inventors: Shinichi Matsufuji, Kawasaki (JP); Momoko Shimizu, Tokyo (JP); Christophe Dumousseaux, Antony (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/413,505

(22) PCT Filed: Jul. 13, 2012

(86) PCT No.: PCT/JP2012/068532
§ 371 (c)(1),
(2), (4) Date: Jun. 10, 2015

(87) PCT Pub. No.: WO2014/010101
PCT Pub. Date: Jan. 16, 2014

(65) Prior Publication Data
US 2015/0290090 A1    Oct. 15, 2015

(51) Int. Cl.
*A61K 8/02* (2006.01)
*A61K 8/29* (2006.01)
*A61K 8/81* (2006.01)
*A61Q 17/04* (2006.01)

(52) U.S. Cl.
CPC .............. *A61K 8/0279* (2013.01); *A61K 8/29* (2013.01); *A61K 8/8152* (2013.01); *A61Q 17/04* (2013.01); *A61K 2800/412* (2013.01); *A61K 2800/413* (2013.01); *A61K 2800/43* (2013.01); *A61K 2800/61* (2013.01); *A61K 2800/621* (2013.01); *A61K 2800/654* (2013.01)

(58) Field of Classification Search
CPC ........ A61K 2800/412; A61K 2800/413; A61K 2800/43; A61K 2800/61; A61K 2800/612; A61K 2800/621; A61K 2800/654; A61K 8/0279; A61K 8/29; A61K 8/8152; A61K 8/29; A61K 8/0241; A61K 8/8117; A61K 8/8147; A61K 8/89; A61Q 17/04
See application file for complete search history.

(56) References Cited

U.S. PATENT DOCUMENTS

| | | |
|---|---|---|
| 2,104,492 A | 1/1938 | Merkel et al. |
| 2,463,264 A | 3/1949 | Graenacher et al. |
| 2,995,540 A | 8/1961 | Duennenberger et al. |
| 3,709,437 A | 1/1973 | Wright |
| 3,937,364 A | 2/1976 | Wright |
| 4,022,351 A | 5/1977 | Wright |
| 4,077,441 A | 3/1978 | Rosen et al. |
| 4,147,306 A | 4/1979 | Bennett |
| 4,184,615 A | 1/1980 | Wright |
| 4,184,625 A | 1/1980 | Johnson et al. |
| 4,217,344 A | 8/1980 | Vanlerberghe et al. |
| 4,246,257 A | 1/1981 | Elliott et al. |
| 4,247,411 A | 1/1981 | Vanlerberghe et al. |
| 4,293,543 A | 10/1981 | Cotte et al. |
| 4,585,597 A | 4/1986 | Lang et al. |
| 4,588,839 A | 5/1986 | Lang et al. |
| 4,598,862 A | 7/1986 | Rice |
| 4,615,467 A | 10/1986 | Grogan et al. |
| 4,617,390 A | 10/1986 | Hoppe et al. |
| 4,699,779 A | 10/1987 | Palinczar |
| 4,772,471 A | 9/1988 | Vanlerberghe et al. |
| 4,797,493 A | 1/1989 | Matsuno et al. |
| 4,814,162 A | 3/1989 | Lang et al. |
| 4,850,517 A | 7/1989 | Ter Stege |
| 4,897,308 A | 1/1990 | Vanlerberghe et al. |
| 4,985,237 A | 1/1991 | Matsuno et al. |
| 5,000,945 A | 3/1991 | Kobayashi et al. |
| 5,021,200 A | 6/1991 | Vanlerberghe et al. |
| 5,030,466 A | 7/1991 | Kageyama et al. |
| 5,064,641 A | 11/1991 | Lang et al. |
| 5,087,729 A | 2/1992 | Matsuno et al. |

(Continued)

FOREIGN PATENT DOCUMENTS

| | | |
|---|---|---|
| CH | 350763 A | 12/1960 |
| CN | 101695466 A | 4/2010 |

(Continued)

OTHER PUBLICATIONS

International Search Report for PCT/JP2012/068532, dated May 3, 2013.
International Search Report for counterpart application PCT/JP2011/052965, dated Jun. 30, 2011.
Contado et al., "TiO2 in Commercial Sunscreen Lotion: Flow Field-Flow Fractionation and ICP-AES Together for Size Analysis," Anal. Chem., XP-002642392, vol. 80, 2008, pp. 7594-7608.
Bacsa_et_al., "CVD Synthesis of Shape and Size Controlled ZnO Nanoparticles for Application as UV Filters," ECS Transactions, The Electrochemical Society, XP009149325, vol. 25, No. 8, Jan. 1, 2009, pp. 1177-1183.

(Continued)

*Primary Examiner* — Shuangyi Abu Ali
(74) *Attorney, Agent, or Firm* — The Marbury Law Group, PLLC

(57) ABSTRACT

The present invention relates to a composite pigment comprising at least one small hollow core particle and optionally at least one large core particle wherein the surface of the small hollow core particle is at least in part covered with at least one coating layer comprising at least one inorganic solid UV filter, and the surface of the large core particle is optionally at least in part covered with at least one coating layer comprising at least one inorganic solid UV filter and/or at least one coloring pigment. The composite pigment according to the present invention can provide enhanced UV filtering effects and safety, and optionally enhanced coloring effects.

17 Claims, No Drawings

(56) References Cited

U.S. PATENT DOCUMENTS

| | | |
|---|---|---|
| 5,166,355 A | 11/1992 | Leistner et al. |
| 5,205,837 A | 4/1993 | Andrean et al. |
| 5,217,709 A | 6/1993 | Lagrange et al. |
| 5,223,533 A | 6/1993 | Forestier et al. |
| 5,236,986 A | 8/1993 | Sakuta |
| 5,237,071 A | 8/1993 | Leistner et al. |
| 5,240,975 A | 8/1993 | Winter et al. |
| 5,346,693 A | 9/1994 | Pilleux et al. |
| 5,362,881 A | 11/1994 | Leistner et al. |
| 5,364,031 A | 11/1994 | Taniguchi et al. |
| 5,373,037 A | 12/1994 | Leistner et al. |
| 5,399,563 A | 3/1995 | Stein et al. |
| 5,412,004 A | 5/1995 | Tachibana et al. |
| 5,501,850 A | 3/1996 | Stein et al. |
| 5,505,935 A | 4/1996 | Guerrero et al. |
| 5,512,094 A | 4/1996 | Linton |
| 5,518,713 A | 5/1996 | Raspanti |
| 5,538,793 A | 7/1996 | Inokuchi et al. |
| 5,585,091 A | 12/1996 | Pelzer et al. |
| 5,643,864 A | 7/1997 | Li et al. |
| 5,656,586 A | 8/1997 | Li et al. |
| 5,677,314 A | 10/1997 | Stein et al. |
| 5,687,521 A | 11/1997 | Carlson et al. |
| 5,688,995 A | 11/1997 | Luther et al. |
| 5,705,169 A | 1/1998 | Stein et al. |
| 5,714,457 A | 2/1998 | Kitsuki et al. |
| 5,730,960 A | 3/1998 | Stein et al. |
| 5,783,554 A | 7/1998 | Li et al. |
| 5,798,331 A | 8/1998 | Anderson et al. |
| 5,811,487 A | 9/1998 | Schulz, Jr. |
| 5,837,793 A | 11/1998 | Harashima et al. |
| 5,846,310 A | 12/1998 | Noguchi et al. |
| 5,849,909 A | 12/1998 | Richard et al. |
| 5,863,886 A | 1/1999 | Tracy et al. |
| 5,872,149 A | 2/1999 | Dralle-Voss et al. |
| 5,888,481 A | 3/1999 | Horn et al. |
| 5,914,310 A | 6/1999 | Li et al. |
| 5,928,630 A | 7/1999 | Richard et al. |
| 5,958,382 A | 9/1999 | Vidal et al. |
| 5,958,431 A | 9/1999 | Brancq et al. |
| 5,961,960 A | 10/1999 | Dilk et al. |
| 6,004,540 A | 12/1999 | Richard et al. |
| 6,007,796 A | 12/1999 | Menzel et al. |
| 6,030,939 A | 2/2000 | Gruning |
| 6,034,271 A | 3/2000 | Kwetkat |
| 6,086,666 A | 7/2000 | Noguchi et al. |
| 6,121,482 A | 9/2000 | Kwetkat et al. |
| 6,156,721 A | 12/2000 | Kwetkat et al. |
| 6,159,455 A | 12/2000 | Habeck et al. |
| 6,225,467 B1 | 5/2001 | Esteghamatian et al. |
| 6,235,270 B1 | 5/2001 | Ishii et al. |
| 6,306,376 B1 | 10/2001 | Philippe |
| 6,322,775 B1 | 11/2001 | Malle et al. |
| 6,342,625 B1 | 1/2002 | Kwetkat et al. |
| 6,365,135 B1 | 4/2002 | Philippe et al. |
| 6,376,679 B2 | 4/2002 | Leduc et al. |
| 6,423,854 B1 | 7/2002 | Philippe et al. |
| 6,432,535 B1 | 8/2002 | Noguchi et al. |
| 6,482,441 B1 | 11/2002 | Hasegawa et al. |
| 6,514,486 B1 | 2/2003 | Tuloup et al. |
| 6,585,983 B1 | 7/2003 | Heinrich et al. |
| 6,645,476 B1 | 11/2003 | Morschhauser et al. |
| 6,710,022 B1 | 3/2004 | Kwetkat et al. |
| 6,710,091 B1 | 3/2004 | Womelsdorf et al. |
| 7,311,897 B2 | 12/2007 | Ehlis et al. |
| 7,393,817 B2 | 7/2008 | Kwetkat et al. |
| 8,083,264 B2 | 12/2011 | Iftime et al. |
| 9,913,782 B2* | 3/2018 | Nagamatsu ............ A61K 8/466 |
| 2001/0028890 A1 | 10/2001 | Miyazaki et al. |
| 2001/0031272 A1 | 10/2001 | Noguchi et al. |
| 2001/0053856 A1 | 12/2001 | Leduc et al. |
| 2002/0005145 A1 | 1/2002 | Sherman |
| 2002/0010179 A1 | 1/2002 | Richard et al. |
| 2003/0101908 A1 | 6/2003 | Hayashi et al. |
| 2003/0105213 A1 | 6/2003 | Hayashi et al. |
| 2003/0215474 A1 | 11/2003 | Miyazaki et al. |
| 2004/0176266 A1 | 9/2004 | Kwetkat et al. |
| 2004/0191191 A1 | 9/2004 | Ehlis et al. |
| 2005/0031653 A1 | 2/2005 | Kwekat et al. |
| 2005/0163730 A1 | 7/2005 | Rosevear et al. |
| 2005/0238979 A1 | 10/2005 | Dumousseaux |
| 2005/0257335 A1 | 11/2005 | Dumousseaux |
| 2005/0257715 A1 | 11/2005 | Dumousseaux |
| 2005/0260146 A1 | 11/2005 | Blin |
| 2006/0018854 A1 | 1/2006 | Dumousseaux et al. |
| 2006/0034875 A1 | 2/2006 | Nakanishi et al. |
| 2006/0039876 A1 | 2/2006 | Dumousseaux et al. |
| 2006/0041054 A1 | 2/2006 | Dumousseaux et al. |
| 2006/0099160 A1 | 5/2006 | Dumousseaux |
| 2007/0098655 A1 | 5/2007 | Schmaus et al. |
| 2007/0104662 A1 | 5/2007 | Satonaka et al. |
| 2007/0134181 A1 | 6/2007 | Shimizu et al. |
| 2007/0155886 A1 | 7/2007 | Sheerin et al. |
| 2008/0044366 A1 | 2/2008 | Dumousseaux |
| 2008/0051472 A1 | 2/2008 | Kwetkat et al. |
| 2009/0185991 A1 | 7/2009 | Spaulding et al. |
| 2009/0186055 A1* | 7/2009 | Dumousseaux ...... A61K 8/8152 424/401 |
| 2009/0324654 A1 | 12/2009 | Polonka et al. |
| 2010/0003204 A1 | 1/2010 | Loy et al. |
| 2010/0055028 A1 | 3/2010 | Scott et al. |
| 2010/0098765 A1 | 4/2010 | Mercado et al. |
| 2010/0272663 A1 | 10/2010 | Pierre et al. |
| 2012/0015016 A1* | 1/2012 | Galdi ...................... A61K 8/72 424/401 |
| 2012/0082708 A1 | 4/2012 | Lee et al. |
| 2013/0084318 A1* | 4/2013 | Ghosh Dastidar ..... B82Y 30/00 424/401 |
| 2013/0259912 A1* | 10/2013 | Suzuki ................ A61K 8/0283 424/401 |
| 2013/0309285 A1 | 11/2013 | Matsufuji et al. |
| 2015/0190320 A1 | 7/2015 | Tachon et al. |
| 2015/0290090 A1 | 10/2015 | Matsufuji et al. |
| 2015/0290109 A1 | 10/2015 | Simonnet et al. |

FOREIGN PATENT DOCUMENTS

| | | |
|---|---|---|
| DE | 676103 C | 5/1939 |
| DE | 4227391 C1 | 9/1993 |
| DE | 19608117 A1 | 9/1997 |
| DE | 19622612 C1 | 10/1997 |
| DE | 19631225 A1 | 2/1998 |
| DE | 19647060 A1 | 5/1998 |
| DE | 19726184 A1 | 12/1998 |
| DE | 19750245 A1 | 5/1999 |
| DE | 19750246 A1 | 5/1999 |
| DE | 19855649 A1 | 6/2000 |
| DE | 19943668 A1 | 3/2001 |
| DE | 19943681 A1 | 3/2001 |
| DE | 10027950 A1 | 12/2001 |
| DE | 10138499 A1 | 2/2003 |
| EP | 0242219 A2 | 10/1987 |
| EP | 0285886 A1 | 10/1988 |
| EP | 0293795 A1 | 12/1988 |
| EP | 0295886 A2 | 12/1988 |
| EP | 0390683 A1 | 10/1990 |
| EP | 0425324 A1 | 5/1991 |
| EP | 0524109 A1 | 1/1993 |
| EP | 0425324 B1 | 10/1993 |
| EP | 0576974 A1 | 1/1994 |
| EP | 0669323 A1 | 8/1995 |
| EP | 0693471 A1 | 1/1996 |
| EP | 0694521 A1 | 1/1996 |
| EP | 0697244 A1 | 2/1996 |
| EP | 0697245 A1 | 2/1996 |
| EP | 0708079 A1 | 4/1996 |
| EP | 0712855 A1 | 5/1996 |
| EP | 0714880 A1 | 6/1996 |
| EP | 0743309 A1 | 11/1996 |
| EP | 0761201 A1 | 3/1997 |
| EP | 0765656 A1 | 4/1997 |
| EP | 0790243 A1 | 8/1997 |
| EP | 0893119 A1 | 1/1999 |

(56) References Cited

FOREIGN PATENT DOCUMENTS

| | | |
|---|---|---|
| EP | 0895779 A1 | 2/1999 |
| EP | 0903342 A1 | 3/1999 |
| EP | 0921126 A1 | 6/1999 |
| EP | 1055642 A2 | 11/2000 |
| EP | 1069142 A1 | 1/2001 |
| EP | 1092421 A2 | 4/2001 |
| EP | 1270686 A2 | 1/2003 |
| FR | 2315991 A1 | 1/1977 |
| FR | 2395023 A1 | 1/1979 |
| FR | 2416008 A1 | 8/1979 |
| FR | 2466492 A1 | 4/1981 |
| FR | 2506156 A1 | 11/1982 |
| FR | 2528420 A1 | 12/1983 |
| FR | 2529887 A1 | 1/1984 |
| FR | 2638354 A1 | 5/1990 |
| FR | 2639347 A1 | 5/1990 |
| FR | 2651126 B1 | 12/1991 |
| FR | 2840806 A1 | 12/2003 |
| FR | 2868694 A1 | 10/2005 |
| FR | 2886853 A1 | 12/2006 |
| GB | 1539625 A | 1/1979 |
| GB | 2286774 A | 8/1995 |
| GB | 2303549 A | 2/1997 |
| GB | 2319523 A | 5/1998 |
| JP | 61-194013 A | 8/1986 |
| JP | S61194009 A | 8/1986 |
| JP | H01158090 A | 6/1989 |
| JP | H01-190625 A | 7/1989 |
| JP | H02295912 A | 12/1990 |
| JP | H03-181584 A | 8/1991 |
| JP | H03-200721 A | 9/1991 |
| JP | H03-243666 A | 10/1991 |
| JP | H04134041 A | 5/1992 |
| JP | H04134042 A | 5/1992 |
| JP | H04134043 A | 5/1992 |
| JP | H04-198124 A | 7/1992 |
| JP | H04-230305 A | 8/1992 |
| JP | H04290882 A | 10/1992 |
| JP | H05-238924 A | 9/1993 |
| JP | H07-149914 A | 6/1995 |
| JP | 08-311003 A | 11/1996 |
| JP | 2628058 B | 7/1997 |
| JP | H09-286928 A | 11/1997 |
| JP | 09-309815 A | 12/1997 |
| JP | 10-017593 A | 1/1998 |
| JP | 10212421 A | 8/1998 |
| JP | H10-338612 A | 12/1998 |
| JP | H10-338616 A | 12/1998 |
| JP | H11-21468 A | 1/1999 |
| JP | 11-060437 A | 3/1999 |
| JP | H11-255630 A | 9/1999 |
| JP | H11-302625 A | 11/1999 |
| JP | 2000-080021 A | 3/2000 |
| JP | 2000-247824 A | 9/2000 |
| JP | 2001-072527 A | 3/2001 |
| JP | 2001-098186 A | 4/2001 |
| JP | 2001-199857 A | 7/2001 |
| JP | 2001-323070 A | 11/2001 |
| JP | 2002-338428 A | 11/2002 |
| JP | 2002-363435 A | 12/2002 |
| JP | 2003-012504 A | 1/2003 |
| JP | 2003-160744 A | 6/2003 |
| JP | 2004-231952 A | 8/2004 |
| JP | 2006-040546 A | 2/2006 |
| JP | 2007-254429 | 4/2007 |
| JP | 2007-126419 A | 5/2007 |
| JP | 2007-277057 A | 10/2007 |
| JP | 2007254429 * | 10/2007 |
| JP | 2008-031138 A | 2/2008 |
| JP | 2009-091203 A | 4/2009 |
| JP | 2010-120871 A | 6/2010 |
| JP | 2011-512376 A | 4/2011 |
| JP | 2011-118046 A | 6/2011 |
| JP | 2011-236193 A | 11/2011 |
| WO | 92/06778 A1 | 4/1992 |
| WO | 9304665 A1 | 3/1993 |
| WO | 9310753 A1 | 6/1993 |
| WO | 9311095 A1 | 6/1993 |
| WO | 9505150 A1 | 2/1995 |
| WO | 96/16930 A1 | 6/1995 |
| WO | 9522959 A2 | 8/1995 |
| WO | 96/14926 A1 | 5/1996 |
| WO | 96/16930 A1 | 6/1996 |
| WO | 96/25384 A1 | 8/1996 |
| WO | 96/25388 A1 | 8/1996 |
| WO | 9703642 A1 | 2/1997 |
| WO | 97/25970 A1 | 7/1997 |
| WO | 97/31890 A1 | 9/1997 |
| WO | 97/35842 A1 | 10/1997 |
| WO | 97/40124 A1 | 10/1997 |
| WO | 9822447 A1 | 5/1998 |
| WO | 9825922 A1 | 6/1998 |
| WO | 99/10318 A1 | 3/1999 |
| WO | 99/22707 A1 | 5/1999 |
| WO | 99/32077 A1 | 7/1999 |
| WO | 02/26211 A1 | 4/2002 |
| WO | 03/024412 A2 | 3/2003 |
| WO | 2004/024798 A1 | 3/2004 |
| WO | 2004/085412 A2 | 10/2004 |
| WO | 2004/105736 A1 | 12/2004 |
| WO | 2006/034982 A1 | 4/2006 |
| WO | 2006/034985 A1 | 4/2006 |
| WO | 2006/034991 A1 | 4/2006 |
| WO | 2006/034992 A1 | 4/2006 |
| WO | 2006/035000 A1 | 4/2006 |
| WO | 2006/035007 A1 | 4/2006 |
| WO | 2009/103602 A1 | 8/2009 |
| WO | 2010/078985 A2 | 7/2010 |
| WO | 2010/098249 A1 | 9/2010 |
| WO | 2011/016139 A1 | 2/2011 |
| WO | 2011/016143 A1 | 2/2011 |
| WO | 2011016144 | 2/2011 |
| WO | 2011/151184 A1 | 12/2011 |
| WO | 2011150034 A2 | 12/2011 |
| WO | WO2011151184 A1 * | 12/2011 ............... C09C 3/08 |
| WO | 2012/069291 A1 | 5/2012 |
| WO | 2014010098 A1 | 1/2014 |
| WO | 2014010100 A1 | 1/2014 |

OTHER PUBLICATIONS

Gera et al., "Mechanical Methods for Dry Particle Coating Processes and Their Applications in Drug Delivery and Development," Recent Patents on Drug Delivery & Formulation, XP55059149, vol. 4, No. 1, Jan. 1, 2010, pp. 58-81.
Todd, Charles., et al., "Volatile Silicone Fluids for Cosmetic Formulations," Cosmetics and Toiletries, vol. 91, 1976, pp. 27-32.
English language abstract for FR 2868694 (Oct. 14, 2005).
English Language Abstract for FR2886853 (Dec. 15, 2006).
International Search Report and Written Opinion for PCT/JP2012/068524. (dated Aug. 5, 2013).
International Search Report for PCT/JP2012/068526 (dated May 2, 2013).
JP2007254429 Machine Translation, 2007.
Non-Final Office Action for co-pending U.S. Appl. No. 14/412,773 (dated Aug. 5, 2015).
English language abstract for DE 19726184 (Dec. 24, 1998).
English language abstract for DE 676103 (May 25, 1939).
English language abstract for EP 0285886 (Oct. 12, 1988).
English language abstract for EP 0390683 (Oct. 3, 1990).
English language abstract for FR 2395023 (Jan. 19, 1979).
English language abstract for JP H01-158090 (Jun. 21, 1989).
English language abstract for JP H02-295912 (Dec. 6, 1990).
English language abstract for JP H04-134041 (May 7, 1992).
English language abstract for JP H04-134042 (May 7, 1992).
English language abstract for JP H04-134043 (May 7, 1992).
English language abstract for JP H04-290882 (Oct. 15, 1992).
English language abstract for JP S61-194009 (Aug. 28, 1986).
International Search Report and Written Opinion for PCT/JP2012/053032 (dated Apr. 24, 2012).

(56) References Cited

OTHER PUBLICATIONS

International Search Report for PCT/JP2011/052965 (dated Jun. 30, 2011).
Japanese Office Action for copending Japanese Application 2013/0535177 (dated Nov. 2, 2015) (with translation).
Restriction Requirement for copending U.S. Appl. No. 13/983,183 (dated Feb. 6, 2015).
Non-Final Office Action for copending U.S. Appl. No. 13/983,183 (dated Jun. 1, 2015).
Final Office Action for copending U.S. Appl. No. 13/983,183 (dated Oct. 15, 2015).
Non-Final Office Action for copending U.S. Appl. No. 13/983,183 (dated Feb. 11, 2016).
Shin-Etsu Technical Data Sheet, KSG-15 (Sep. 12, 2012).
Shin-Etsu Technical Data Sheet, KSG-16 (Sep. 12, 2012).
Shin-Etsu Technical Data Sheet, KSG-18A (May 9, 2013).
Japanese Office Action for copending Japanese Application 2015/521150 (dated Feb. 22, 2016) (with translation).
European Patent Office Action for copending European Application No. 12709183 (dated Feb. 24, 2016).
Tsugio, Sato et al., "Synthesis and UV-shielding Properties of Calcia-Doped Ceria Nanoparticles Coated with Amorphous Silica," Solid State Ionics, 172, (2004), pp. 377-382.
Restriction Requirement for copending U.S. Appl. No. 14/412,773 (dated Apr. 20, 2015).
Non-Final Office Action for copending Application No. 14/412,773 (dated Aug. 5, 2015).
Restriction Requirement for copending U.S. Appl. No. 14/412,777 (dated Dec. 21, 2015).
Non-Final Office Action for copending U.S. Appl. No. 14/412,77 (dated Mar. 10, 2016).
English language Abstract for DE 19622612C1 (Oct. 23, 1997).
English language Abstract for DE 19631225 A1 (Feb. 5, 1998).
English language Abstract for DE 19647060 A1 (May 20, 1998).
English language Abstract for DE 19750245 A1 (May 20, 1999).
English language Abstract for DE 19750246 A1 (May 20, 1999).
English language Abstract for DE 19943681 A1 (Mar. 15, 2001).
English language Abstract for EP 0425324 A1 (May 2, 1991).
English language Abstract for FR 2651126 B1 (Dec. 6, 1991).
English language Abstract for FR 2840806 A1 (Dec. 19, 2003).
English language Abstract for JPH01-190625A (Jul. 31, 1989).
English language Abstract for JPH03-181584A (Aug. 7, 1991).
English language Abstract for JPH03-200721A (Sep. 2, 1991).
English language Abstract for JPH03-243666A (Oct. 30, 1991).
English language Abstract for JP05-238924A (Sep. 17, 1993).
English language Abstract for JPH07-149914A (Jun. 13, 1995).
English language machine translation of JP8-311003A (Nov. 26, 1996).
English language Abstract for JPH09-286928A (Nov. 4, 1997).
English language machine translation of JP10-017593A (Jan. 20, 1998).
English language Abstract for JP10-338612A (Dec. 22, 1998).
English language Abstract for JP10-338616A (Dec. 22, 1998).
English language machine translation of JP11-060437A (Mar. 2, 1999).
English language Abstract for JPH11-255630A (Sep. 21, 1999).
English language Abstract for JP2000-080021A (Mar. 21, 2000).
English language Abstract for JP2003-012504A (Jan. 15, 2003).
English language Abstract for JP2004-231952A (Aug. 19, 2004).
English language Abstract for JP2006-040546A (Feb. 9, 2006).
English language Abstract for JP2009-091203A (Apr. 30, 2009).
English language Abstract for JP2010-120871A (Jun. 3, 2010).
English language Abstract for JP2011-118046A (Jun. 16, 2011).
English language Abstract for JP2011-236193A (Nov. 24, 2011).
Non-Final Office Action for copending U.S. Appl. No. 14/412,773 (dated Jan. 29, 2016).
Japanese Office Action for JP 2015-521147, dated Mar. 7, 2016.
Japanese Office Action for JP 2015-521149, dated Mar. 7, 2016.
Chinese Office Action for CN 201280074100.8, dated Mar. 31, 2016.
English language Abstract for EP 0425324 B1 (Oct. 27, 1993).
Notice of Allowance for counterpart JP Application No. 2015-521150, dated Jan. 30, 2017.
Office Action for counterpart Application JP2013-535177, dated Oct. 2, 2017.
European Office Action received in connection with European Application No. EP12745921.2; dated Jul. 4, 2017.
Point of Interest! (Mineral-make up ingredients: Boron nitride: http://swiftcraftymonkey.blogspot.com/2009/08/mineral-make-up-ingredients-boron.html) Aug. 16, 2009.
Advisory Action Issued in related U.S. Appl. No. 14/412,777 dated Jan. 19, 2018.
Non Final Office Action dated Feb. 14, 2018 in related U.S. Appl. No. 14/412,773, filed Jan. 5, 2015.
Office Action for counterpart U.S. Appl. No. 14/412,777, dated Apr. 10, 2018.
TSD BN Product Cosmetics (http://www.topspindesign.com/business/bn_cosmetic.htm 2010).
Non-Final Office Action for copending U.S. Appl. No. 15/404,563, dated Dec. 4, 2018.
Non-Final Office Action for co-pending U.S. Appl. No. 15/404,563, dated Sep. 20, 2019.
Liang, H. et al., "UV Protection Effectiveness of Plastic Particles Coated with Titanium Dioxide by Rotational Impact Blending," Institution of Chemical Engineers, Trans IChemE, vol. 78, Part A, Jan. 2000, pp. 49-54.
Final Office Action for copending U.S. Appl. No. 14/412,773, dated Feb. 3, 2020.
Final Office Action for copending U.S. Appl. No. 15/404,563, dated Feb. 13, 2020.
Jaroenworaluck, A. et al., "Characteristics of Silica-Coated TiO2 and its UV Absorption for SunScreen Cosmetic Applications," Surface and Interface Analysis, vol. 38, Issue 4, Mar. 29, 2006, pp. 473-477.
English Abstract for "Sunscreen: According to the current state of knowledge zinc oxide as UV filter is safe, BfR Opinion No. 037/2010, Jun. 18, 2010, Internet, URL , <http://www.bfr.bund.de/cm/206/sonnenschutzmittel_zinkoxid_als_uv_filter_ist_nach_derzeitigem_kenntnisstand_gesundheitlich_unbedenklich.pdf".
Partial Machine Translation of Opposition to EP 2 872 106 B1, dated May 10, 2021.

\* cited by examiner

COMPOSITE PIGMENT AND METHOD FOR PREPARING THE SAME

This is a national stage application of PCT/JP2012/068532, filed internationally on Jul. 13, 2012.

TECHNICAL FIELD

The present invention relates to a composite pigment comprising a small hollow core particle which is at least partially covered by inorganic solid UV filters, and in particular further containing a large core particle, as well as a method for preparing the composite pigment.

BACKGROUND ART

Many cosmetics include one or more UV filters in order to shield UV rays. In particular, skin cosmetics commonly include inorganic solid UV filters such as fine particles of $TiO_2$ for protecting the skin from UV rays.

However, inorganic solid UV filters such as fine particles of $TiO_2$ can easily aggregate and have poor dispersibility. Therefore, it is often difficult to uniformly disperse them in the form of primary particles in cosmetics. Therefore, the UV filtering property of cosmetics including inorganic solid UV filters is difficult to be enhanced.

JP-A-2007-254429 discloses composite pigments comprising a relatively large core particle covered with inorganic solid UV filters.

The composite pigments based on a relatively large core particle covered with inorganic solid UV filters can provide improved UV filtering effects, because the aggregation of the inorganic solid UV filters can be prevented.

DISCLOSURE OF INVENTION

However, the UV filtering effects provided by the above composite pigments are still insufficient, and thus further improvement in the UV filtering effects is desired.

Furthermore, there are some risks that fine particles of inorganic solid UV filter(s) may have adverse effects on the skin, and the inorganic solid UV filter(s) can irritate the skin when it or they contact the skin.

Thus, an objective of the present invention is to provide a novel composite pigment which is based on inorganic solid UV filter(s) and which can provide better UV filtering effects.

Another objective of the present invention is to reduce the risk of fine particles of inorganic solid UV filter(s), in order to reduce or prevent possible adverse effects on the skin by the inorganic solid UV filter(s), while providing better UV filtering effects.

Any of the above objectives of the present invention can be achieved by a composite pigment comprising:

at least one small hollow core particle with a mean particle size of more than 100 nm and less than 1 μm, preferably less than 600 nm, and more preferably less than 400 nm, wherein the surface of the small hollow core particle is at least in part covered with at least one coating layer comprising at least one inorganic solid UV filter, and the said small particle contains at least one organic polymer.

The coating layer on the small hollow core particle may include at least one coloring pigment.

The inorganic solid UV filter may be selected from the group consisting of silicon carbide, metal oxides, and mixtures thereof. It is preferable that the inorganic solid UV filter is titanium oxide.

The inorganic solid UV filter may have a mean particle size of 1 nm to 50 nm, preferably 5 nm to 40 nm, and more preferably 10 nm to 30 nm.

The inorganic solid UV filter may have at least one coating.

The inorganic solid UV filter may comprise at least one compound selected from the group consisting of alumina, silica, aluminum hydroxide, silicones, silanes, fatty acids or salts thereof, fatty alcohols, lecithin, amino acids, polysaccharides, proteins, alkanolamines, waxes, (meth)acrylic polymers, organic UV filters, and (per)fluoro compounds.

The coating layer on the small hollow core particle may have a thickness of 1 nm to 50 nm, preferably 5 nm to 40 nm, and more preferably 10 nm to 30 nm.

The coloring pigment may be selected from the group consisting of titanium dioxide, zirconium oxide, cerium oxide, zinc oxide, iron oxide, chromium oxide, manganese violet, ultramarine blue, chromium hydrate, ferric blue, aluminum powder, copper powder, silver powder, gold powder, barium sulfate, carbon black, pigments of D&C type, lakes, pearlescent pigments, silica, and mixtures thereof.

The coating layer on the small hollow core particle may further comprise at least one additional UV filter, in particular at least one organic UV filter.

The small hollow core particle may further comprise at least one inorganic material.

The inorganic material may be selected from the group consisting of mica, synthetic mica, talc, sericite, boron nitride, glass flake, calcium carbonate, barium sulfate, titanium oxide, hydroxyapatite, silica, silicate, zinc oxide, magnesium sulfate, magnesium carbonate, magnesium trisilicate, aluminum oxide, aluminum silicate, calcium silicate, calcium phosphate, magnesium oxide, bismuth oxychloride, kaolin, hydrotalcite, mineral clay, synthetic clay, iron oxide, and mixtures thereof.

The organic polymer of the small hollow core particle may be selected from the group consisting of poly(meth)acrylates, polyamides, silicones, polyurethanes, polyethylenes, polypropylenes, polystyrenes, copolystyrenes, polyhydroxyalkanoates, polycaprolactams, poly(butylene) succinates, polysaccharides, polypeptides, polyvinyl alcohols, polyvinyl resins, fluoropolymers, wax, amidosulfonic acid polyvalent metal salts, acylated amino acids, and mixtures thereof.

In particular, as the organic polymer, copolystyrene is preferable. Furthermore, styrene/acrylate copolymer, and cross-linked styrene/methyl methacrylate copolymer are more preferable.

In a preferred embodiment, the composite pigment according to the invention may further contain at least one large core particle with a mean particle size of 2 μm or more, preferably 3 μm or more, more preferably 4 μm or more, and even more preferably 5 μm or more, wherein the surface of the large core particle is optionally at least in part covered with at least one coating layer comprising at least one inorganic solid UV filter and/or at least one coloring pigment.

The weight ratio of the small hollow core particle(s) to the large core particle(s) may be 10:90 to 90:10, preferably 20:80 to 80:20, and more preferably 30:70 to 70:30.

The weight ratio of the small hollow core particle(s) to the inorganic solid UV filter(s) may be 10:90 to 90:10, preferably 30:70 to 70:30, and more preferably 40:60 to 50:50.

The weight ratio of the small hollow core particle(s)/the large core particle(s)/the inorganic solid UV filter(s) may be 20:50:30 to 50:20:30, preferably 35:15:50 to 15:35:50, and more preferably 10:20:70 to 20:10:70.

The large core particle may comprise at least one inorganic material and/or at least one organic material, preferably at least one organic material.

The inorganic material of the large core particle may be selected from the group consisting of mica, synthetic mica, talc, sericite, boron nitride, glass flake, calcium carbonate, barium sulfate, titanium oxide, hydroxyapatite, silica, silicate, zinc oxide, magnesium sulfate, magnesium carbonate, magnesium trisilicate, aluminum oxide, aluminum silicate, calcium silicate, calcium phosphate, magnesium oxide, bismuth oxychloride, kaolin, hydrotalcite, mineral clay, synthetic clay, iron oxide, and mixtures thereof.

The organic material of the large core particle may be selected from the group consisting of poly(meth)acrylates, polyamides, silicones, polyurethanes, polyethylenes, polypropylenes, polystyrenes, copolystyrenes, polyhydroxylkanoates, polycaprolactams, poly(butylene)succinates, polysaccharides, polypeptides, polyvinyl alcohols, polyvinyl resins, fluoropolymers, wax, amidosulfonic acid polyvalent metal salts, acylated amino acids, and mixtures thereof.

In particular, polymethacrylate is preferable as the organic material for the large core particle. Methylmethacrylate polymer is more preferable.

In a preferred embodiment of the present invention, the small hollow core particle may comprise at least one copolystyrene, preferably styrene/acrylate copolymer and/or cross-linked styrene/methyl methacrylate copolymer;

the large core particle may comprise at least one poly (meth)acrylate, preferably methyl methacrylate polymer; and the small hollow core and large core particles may be at least in part covered with at least one coating layer comprising metal oxide, preferably titanium oxide.

The composite pigment according to the present invention can be prepared by a method for preparing a composite pigment, comprising a step of subjecting:

at least one small hollow core particle with a mean particle size of more than 100 nm and of less than 1 μm, preferably less than 600 nm, and more preferably less than 400 nm, wherein the small hollow core particle comprises at least one organic polymer;

optionally at least one large core particle with a mean particle size of 2 μm or more, preferably 3 μm or more, more preferably 4 μm or more, and even more preferably 5 μm or more;

at least one inorganic solid UV filter; and optionally at least one coloring pigment and/or at least one additional UV filter to a mechanochemical fusion process.

Another objective of the present invention is to provide a cosmetic composition or a cosmetic agent with advantageous cosmetic and/or practical effects by using the composite pigment according to the present invention.

The above objective can be achieved by incorporating the composite pigment according to the present invention into a cosmetic composition or a cosmetic agent for the photoprotection against UV radiation.

Thus, for example, the composite pigment according to the present invention can be contained in a cosmetic composition, in particular in the form of a liquid, powdery or aerosol foam cosmetic composition.

BEST MODE FOR CARRYING OUT THE INVENTION

After diligent research, the inventors have discovered that it is possible to obtain a new composite pigment providing enhanced UV filtering effects.

The new composite pigment according to the present invention comprises at least one small hollow core particle with a mean particle size of less than 1 μm wherein the surface of the small hollow core particle is at least in part covered with at least one layer comprising at least one inorganic solid UV filter, wherein the small hollow core particle comprises at least one organic polymer.

Surprisingly, it was discovered that the use of a small core particle with a mean particle size of less than 1 μm, wherein the small core particle contains at least one organic polymer, and optionally of a large core particle, can provide a coating including inorganic solid UV filter(s) to the surface of the small core particle, which thereby results in better UV filtering effects than a single particle including inorganic solid UV filter(s), and that the UV filtering effects can be further enhanced when using a hollow particle as the small core particle.

Since particles of inorganic solid UV filter(s) are firmly bonded on the small hollow particles, a large amount of free inorganic UV filter(s) cannot directly contact with the skin. Accordingly, the composite pigment according to the present invention is safer than the bulk of inorganic solid UV filters.

Further, the composite pigment according to the present invention can provide a better feeling on use, because fine particles of inorganic solid UV filter(s) are firmly fixed on the core particles so that it is possible to reduce free fine particles which have a high friction coefficient such that they do not easily spread on the skin and provide an unpleasant feeling on use.

Furthermore, a cosmetic composition or a cosmetic agent comprising the composite pigment according to the present invention can exert advantageous cosmetic and/or practical effects due to the inclusion of the composite pigment according to the present invention. For example, the cosmetic composition according to the present invention has better UV shielding effects. In addition, if the cosmetic composition is in the form of a powder, it also has a smooth feeling on use due to reduced friction, superior hiding effects for skin defects such as pores and fine lines, matt effects and good compactability such that it is difficult to chip away. On the other hand, if the cosmetic composition is in the form of a liquid, it also has good visual optical effects such as matt and haze effects.

Hereafter, each of the elements constituting the composite pigment and cosmetic composition according to the present invention will be described in a detailed manner.

(Small Core Particle)

The small core particle to be used for the composite pigment according to the present invention is not limited, as long as the small core particle is hollow and has a mean particle size or a mean particle diameter of more than 100 nm and less than 1 μm, preferably less than 600 nm, and more preferably less than 400 nm.

The mean particle size or mean particle diameter here is an arithmetic mean diameter, and can be determined, for example, by calculating the average of the dimensions of one hundred particles chosen on an image obtained with a scanning electron microscope.

The small hollow core particle can be in any shape. For example, it is possible to use a small hollow core particle in the form of a plate with an aspect ratio of at least 5, preferably more than 10, more preferably more than 20, and more preferably more than 50. The aspect ratio can be determined by the average thickness and the average length according to the formula: aspect ratio=length/thickness.

If a plate-like particle is used for the present invention, it is preferable that the plate-like particle has a length ranging from more than 100 nm to less than 1 μm, preferably less than 600 nm, and more preferably less than 400 nm.

In a preferred embodiment, the small hollow core particle has a spherical shape.

The material of the small hollow core particle is not limited. The material of the small hollow core particle comprises at least one organic polymer, and may be further comprise at least one inorganic material.

The organic polymer of the small hollow core particle may be selected from the group consisting of poly(meth) acrylates, polyamides, silicones, polyurethanes, polyethylenes, polypropylenes, polystyrenes, copolystyrenes, polyhydroxyalkanoates, polycaprolactams, poly(butylene) succinates, polysaccharides, polypeptides, polyvinyl alcohols, polyvinyl resins, fluoropolymers, wax, amidosulfonic acid polyvalent metal salts, acylated amino acids, and mixtures thereof.

As fluoropolymers, for example, PTFE may be used. As amidosulfonic acid polyvalent metal salts, for example, N-lauroyltaurine calcium may be used. As acylated amino acids, lauroyllysine may be used. Polyamides such as Nylon®, polyhydroxyalkanoates such as polylactic acids, poly(meth)acrylates such as polymethylmethacrylates, silicones, and mixtures thereof are more preferable.

In particular, as the organic polymer, copolystyrene is preferable, and styrene/acrylate copolymer, and cross-linked styrene/methyl methacrylate copolymer are more preferable. Thus, as the small hollow core particles, for example, Sunspheres (small hollow particles made from styrene/acrylate copolymer) marketed by Rohm and Haas, as well as SX859(A) and SX866(B) (small hollow particles made form cross-linked styrene/methyl methacrylate copolymer) marketed by JSR Corp. in Japan, are preferable.

Preferably, the inorganic material can be selected from the group consisting of mica, synthetic mica, talc, sericite, boron nitride, glass flakes, calcium carbonate, barium sulfate, titanium oxide, hydroxyapatite, silica, silicate, zinc oxide, magnesium sulfate, magnesium carbonate, magnesium trisilicate, aluminum oxide, aluminum silicate, calcium silicate, calcium phosphate, magnesium oxide, bismuth oxychloride, kaolin, hydrotalcite, mineral clay, synthetic clay, iron oxide, and mixtures thereof. In particular, natural mica, synthetic mica, sericite, kaolin, talc and mixtures thereof are preferable.

The inorganic material and/or organic polymer may be porous. The porosity of the material may be characterized by a specific surface area of from 0.05 $m^2/g$ to 1,500 $m^2/g$, more preferably from 0.1 $m^2/g$ to 1,000 $m^2/g$, and more preferably from 0.2 $m^2/g$ to 500 $m^2/g$ according to the BET method.

The small hollow core particle may or may not be coated beforehand.

In a particular embodiment, the small hollow core particle is originally coated. The material of an original coating of the small hollow core particle is not limited, but an organic material such as an amino acid, an N-acylamino acid, an amido, a silicone and a modified silicone, may be preferable.

As the organic material, mention may be made of lauroyl lysine and acryl-modified silicone.

(Layer on Small Core Particle)

The small hollow core particle is at least partially covered with at least one layer comprising at least one inorganic solid UV filter. The layer may be referred to as a coating layer. Preferably, 10% or more of the surface of the small hollow core particle can be covered by the coating layer(s). More preferably, 50% or more of the surface of the small hollow core particle can be covered by the coating layer(s). More preferably, 80% or more of the small hollow core particle can be covered by the coating layer(s). Most preferably, the entire surface of the small hollow core particle can be covered by the coating layer(s).

The thickness of the coating layer may vary depending on several factors such as the size of the small hollow core particle. Typically, the thickness of the coating layer may range from 1 nm to 50 nm, preferably 5 nm to 40 nm, and more preferably from 10 nm to 30 nm.

If there are two or more coating layers on the small hollow core particle, the thickness and the composition of the coating layers may be the same as or different from each other.

The coating layer(s) may comprise, other than the inorganic solid UV filter(s), any additional material(s) such as coloring pigment(s) and/or additional UV filter(s), preferably organic UV filter(s). The additional material(s) may be present in an amount ranging from 1 to 50 wt % relative to the total weight of the additional material(s) and the inorganic solid UV filter(s).

(Inorganic Solid UV Filter)

As described above, the coating layer(s) on the small hollow core particle comprises at least one inorganic solid UV filter. If two or more inorganic solid UV filters are used, they may be the same or different, preferably the same.

The inorganic solid UV filter used for the present invention may be active in the UV-A and/or UV-B region, preferably in the UV-B region or in the UV-A and UV-B region. It is preferable that the active UV filtering region of the inorganic solid UV filter and that of the additional UV filter be complementary to each other, in order to provide comprehensive UV protection. For example, it is preferable that the inorganic solid UV filter be active at least in the UV-B region and the additional UV filter be active at least in the UV-A region. The inorganic solid UV filter may be hydrophilic and/or lipophilic. The inorganic solid UV filter is completely insoluble in solvents such as water and ethanol commonly used in cosmetics. The term "solid" means solid at 25° C. under 1 atm.

It is preferable that the inorganic solid UV filter be in the form of a fine particle such that the mean (primary) particle diameter thereof ranges from 1 nm to 50 nm, preferably 5 nm to 40 nm, and more preferably 10 nm to 30 nm. The mean (primary) particle size or mean (primary) particle diameter here is an arithmetic mean diameter.

The inorganic solid UV filter may be selected from the group consisting of silicon carbide, metal oxides which may or may not be coated, and mixtures thereof.

Preferably, the inorganic solid UV filters are selected from pigments (mean size of the primary particles: generally from 5 nm to 50 nm, preferably from 10 nm to 50 nm) formed of metal oxides, such as, for example, pigments formed of titanium oxide (amorphous or crystalline in the rutile and/or anatase form), iron oxide, zinc oxide, zirconium oxide or cerium oxide, which are all UV photoprotective agents well known per se. Preferably, the inorganic solid UV filters are selected from titanium oxide, zinc oxide, and more preferably titanium oxide.

The inorganic solid UV filter may or may not be coated. The inorganic solid UV filter may have at least one coating. The coating may comprise at least one compound selected from the group consisting of alumina, silica, aluminum hydroxide, silicones, silanes, fatty acids or salts thereof (such as sodium, potassium, zinc, iron or aluminum salts), fatty alcohols, lecithin, amino acids, polysaccharides, proteins, alkanolamines, waxes such as beeswax, (meth)acrylic polymers, organic UV filters, and (per)fluoro compounds.

It is preferable for the coating to include at least one organic UV filter. As the organic UV filter in the coating, a dibenzoylmethane derivative such as butyl methoxydibenzoylmethane (Avobenzone) and 2,2'-Methylenebis[6-(2H-Benzotriazol-2-yl)-4-(1,1,3,3-Tetramethyl-Butyl)Phenol] (Methylene Bis-Benzotriazolyl Tetramethylbutylphenol) marketed as "TINOSORB M" by BASF may be preferable.

In a known manner, the silicones in the coating(s) may be organosilicon polymers or oligomers comprising a linear or cyclic and branched or cross-linked structure, of variable molecular weight, obtained by polymerization and/or polycondensation of suitable functional silanes and essentially composed of repeated main units in which the silicon atoms are connected to one another via oxygen atoms (siloxane bond), optionally substituted hydrocarbon radicals being connected directly to said silicon atoms via a carbon atom.

The term "silicones" also encompasses silanes necessary for their preparation, in particular alkylsilanes.

The silicones used for the coating(s) can preferably be selected from the group consisting of alkylsilanes, polydialkylsiloxanes and polyalkylhydrosiloxanes. More preferably still, the silicones are selected from the group consisting of octyltrimethylsilane, polydimethylsiloxanes and polymethylhydrosiloxanes.

Of course, the inorganic solid UV filters made of metal oxides may, before their treatment with silicones, have been treated with other surfacing agents, in particular with cerium oxide, alumina, silica, aluminum compounds, silicon compounds or their mixtures.

The coated inorganic solid UV filter may have been prepared by subjecting the inorganic solid UV filter to one or more surface treatments of a chemical, electronic, mechanochemical and/or mechanical nature with any of the compounds as described above, as well as polyethylenes, metal alkoxides (titanium or aluminum alkoxides), metal oxides, sodium hexametaphosphate, and those shown, for example, in Cosmetics & Toiletries, February 1990, Vol. 105, pp. 53-64.

The coated inorganic solid UV filters may be titanium oxides coated:

with silica, such as the product "Sunveil" from Ikeda;

with silica and with iron oxide, such as the product "Sunveil F" from Ikeda;

with silica and with alumina, such as the products "Microtitanium Dioxide MT 500 SA" from Tayca, "Tioveil" from Tioxide, and "Mirasun TiW 60" from Rhodia;

with alumina, such as the products "Tipaque TTO-55 (B)" and "Tipaque TTO-55 (A)" from Ishihara, and "UVT 14/4" from Kemira;

with alumina and with aluminum stearate, such as the product "Microtitanium Dioxide MT 100 T, MT 100 TX, MT 100 Z or MT-01" from Tayca, the products "Solaveil CT-10 W" and "Solaveil CT 100" from Uniqema, and the product "Eusolex T-AVO" from Merck;

with alumina and with aluminum laurate, such as the product "Microtitanium Dioxide MT 100 S" from Tayca;

with iron oxide and with iron stearate, such as the product "Microtitanium Dioxide MT 100 F" from Tayca;

with zinc oxide and with zinc stearate, such as the product "BR351" from Tayca;

with silica and with alumina and treated with a silicone, such as the products "Microtitanium Dioxide MT 600 SAS", "Microtitanium Dioxide MT 500 SAS" and "Microtitanium Dioxide MT 100 SAS" from Tayca;

with silica, with alumina and with aluminum stearate and treated with a silicone, such as the product "STT-30-DS" from Titan Kogyo;

with silica and treated with a silicone, such as the product "UV-Titan X 195" from Kemira;

with alumina and treated with a silicone, such as the products "Tipaque TTO-55 (S)" from Ishihara or "UV Titan M 262" from Kemira;

with triethanolamine, such as the product "STT-65-S" from Titan Kogyo;

with stearic acid, such as the product "Tipaque TTO-55 (C)" from Ishihara; or with sodium hexametaphosphate, such as the product "Microtitanium Dioxide MT 150 W" from Tayca.

Other titanium oxide pigments treated with a silicone are preferably $TiO_2$ treated with octyltrimethylsilane and for which the mean size of the individual particles is from 25 and 40 nm, such as that marketed under the trademark "T 805" by Degussa Silices, $TiO_2$ treated with a polydimethylsiloxane and for which the mean size of the individual particles is 21 nm, such as that marketed under the trademark "70250 Cardre UF $TiO_2Si_3$" by Cardre, anatase/rutile $TiO_2$ treated with a polydimethylhydrosiloxane and for which the mean size of the individual particles is 25 nm, such as that marketed under the trademark "Microtitanium Dioxide USP Grade Hydrophobic" by Color Techniques.

Preferably, the following coated $TiO_2$ can be used as the coated inorganic UV filter:

Stearic acid (and) Aluminum Hydroxide (and) $TiO_2$, such as the product "MT-100 TV" from Tayca, with a mean primary particle diameter of 15 nm;

Dimethicone (and) Stearic Acid (and) Aluminum Hydroxide (and) $TiO_2$, such as the product "SA-TTO-S4" from Miyoshi Kasei, with a mean primary particle diameter of 15 nm;

Silica (and) $TiO_2$, such as the product "MT-100 WP" from Tayca, with a mean primary particle diameter of 15 nm;

Dimethicone (and) Silica (and) Aluminum Hydroxide (and) $TiO_2$, such as the product "MT-Y02" and "MT-Y-110 M3S" from Tayca, with a mean primary particle diameter of 10 nm;

Dimethicone (and) Aluminum Hydroxide (and) $TiO_2$, such as the product "SA-TTO-S3" from Miyoshi Kasei, with a mean primary particle diameter of 15 nm;

Dimethicone (and) Alumina (and) $TiO_2$, such as the product "UV TITAN M170" from Sachtleben, with a mean primary particle diameter of 15 nm; and Silica (and) Aluminum Hydroxide (and) Alginic Acid (and) $TiO_2$, such as the product "MT-100 AQ" from Tayca, with a mean primary particle diameter of 15 nm.

In terms of UV filtering ability, $TiO_2$ coated with at least one organic UV filter is more preferable. For example, Avobenzone (and) Stearic Acid (and) Aluminum Hydroxide (and) $TiO_2$, such as the product "HXMT-100ZA" from Tayca, with a mean primary particle diameter of 15 nm, can be used.

The uncoated titanium oxide pigments are, for example, marketed by Tayca under the trademarks "Microtitanium Dioxide MT500B" or "Microtitanium Dioxide MT600B", by Degussa under the trademark "P 25", by Wacker under the trademark "Oxyde de titane transparent PW", by Miyoshi Kasei under the trademark "UFTR", by Tomen under the trademark "ITS" and by Tioxide under the trademark "Tioveil AQ".

The uncoated zinc oxide pigments are, for example:
those marketed under the trademark "Z-cote" by Sunsmart;
those marketed under the trademark "Nanox" by Elementis; and
those marketed under the trademark "Nanogard WCD 2025" by Nanophase Technologies.

The coated zinc oxide pigments are, for example:
those marketed under the trademark "Oxide Zinc CS-5" by Toshiba (ZnO coated with polymethylhydrosiloxane);
those marketed under the trademark "Nanogard Zinc Oxide FN" by Nanophase Technologies (as a 40% dispersion in Finsolv TN, $C_{12}$-$C_{15}$ alkyl benzoate);
those marketed under the trademark "Daitopersion Zn-30" and "Daitopersion Zn-50" by Daito (dispersions in oxyethylenated polydimethylsiloxane/cyclopolymethylsiloxane comprising 30% or 50% of zinc nano-oxides coated with silica and polymethylhydrosiloxane);
those marketed under the trademark "NFD Ultrafine ZnO" by Daikin (ZnO coated with phosphate of perfluoroalkyl and a copolymer based on perfluoroalkylethyl as a dispersion in cyclopentasiloxane);
those marketed under the trademark "SPD-Z1" by Shin-Etsu (ZnO coated with a silicone-grafted acrylic polymer dispersed in cyclodimethylsiloxane);
those marketed under the trademark "Escalol Z100" by ISP (alumina-treated ZnO dispersed in an ethylhexyl methoxycinnamate/PVP-hexadecene copolymer/methicone mixture); and
those marketed under the trademark "Fuji ZnO-SMS-10" by Fuji Pigment (ZnO coated with silica and polymethylsilsesquioxane); those marketed under the trademark "Nanox Gel TN" by Elementis (ZnO dispersed at 55% in $C_{12}$-$C_{15}$ alkyl benzoate with hydroxystearic acid polycondensate).

The uncoated cerium oxide pigments are marketed, for example, under the trademark "Colloidal Cerium Oxide" by Rhone-Poulenc.

The uncoated iron oxide pigments are, for example, marketed by Arnaud under the trademarks "Nanogard WCD 2002 (FE 45B)", "Nanogard Iron FE 45 BL AQ", "Nanogard FE 45R AQ" and "Nanogard WCD 2006 (FE 45R)", or by Mitsubishi under the trademark "TY-220".

The coated iron oxide pigments are, for example, marketed by Arnaud under the trademarks "Nanogard WCD 2008 (FE 45B FN)", "Nanogard WCD 2009 (FE 45B 556)", "Nanogard FE 45 BL 345" and "Nanogard FE 45 BL" or by BASF under the trademark "Oxyde de fer transparent".

Mention may also be made of mixtures of metal oxides, in particular of titanium dioxide and of cerium dioxide, including a mixture of equal weights of titanium dioxide coated with silica and of cerium dioxide coated with silica marketed by Ikeda under the trademark "Sunveil A", and also a mixture of titanium dioxide and of zinc dioxide coated with alumina, with silica and with silicone, such as the product "M 261" marketed by Kemira, or coated with alumina, with silica and with glycerol, such as the product "M 211" marketed by Kemira.

Coated inorganic solid UV filters are preferable, because the UV filtering effects of the inorganic solid UV filters can be enhanced. In addition, the coating(s) may function as a binder for fixing the UV filters on a small core particle.

If the inorganic solid UV filter(s) in the form of fine particles is/are used, the composite pigment according to the present invention has an effect of not providing a white appearance but a transparent or clear appearance, because the fine particles of the inorganic solid UV filters do not aggregate but spread on the core particle. It should be noted that free fine particles of inorganic solid UV filter(s) easily aggregate to give a white appearance to the skin.

The inorganic solid UV filter(s) may be used in the composite pigment according to the present invention in proportions such that the weight ratio of the small hollow core particle(s) to the inorganic solid UV filter(s) is 10:90 to 90:10, preferably 30:70 to 70:30, and more preferably 40:60 to 50:50.

(Coloring Pigment)

As described above, the coating layer(s) on the small hollow core particle may comprise at least one coloring pigment.

The term "coloring pigment(s)" should be understood as meaning white or colored, inorganic or organic particle(s) of any shape which is/are insoluble and is/are intended to color a composition comprising them.

If coloring pigment(s) is/are used, the composite pigment according to the present invention has an effect of providing a clearer appearance with high chroma, because the coloring pigments do not aggregate but spread on the substrate. It should be noted that free coloring pigments easily aggregate to give a dark appearance with low chroma to the skin. Therefore, the color of the cosmetics including coloring pigments can be opaque and dark. On the other hand, the composite pigment according to the present invention can provide clear and bright color tone.

The pigments can be white or colored, inorganic and/or organic and generally have a mean particle size greater or equal to 1 µm.

Among the inorganic pigments that may be used, non-limiting mention may be made of titanium dioxide, optionally surface treated, zirconium or cerium oxide, as well as zinc, (black, yellow or red) iron or chromium oxide, manganese violet, ultramarine blue, chromium hydrate and ferric blue, barium sulfate, or metal powders, such as aluminum, copper, silver or gold powder.

The particle size of the coloring pigment is not limited. In a particular embodiment, the coloring pigment may have a mean particle size of from 100 nm to less than 1 µm, preferably from 100 nm to less than 500 nm, and more preferably from 100 nm to less than 300 nm.

Since particles of coloring pigment(s) can be firmly bonded on the small hollow core particle, the coloring pigment(s) cannot penetrate into the skin via pores on the skin. In addition, even if the coloring pigment(s) irritate, a large amount of the coloring pigment(s) cannot directly contact with the skin, because they are present only on the small hollow core particle. Accordingly, the composite pigment according to the present invention is safer than the bulk of coloring pigments.

Among organic pigments that may be used, non-limiting mention may be made of carbon black, pigments of D&C type and lakes, such as lakes-based on cochineal carmine and on barium, strontium, calcium or aluminum. For example, Red 202 (Calcium bis[2-(3-carboxy-2-hydroxy-nephthylazo)-5-methylbenzenesulfonate) may be used as the pigment of D&C type.

Preferably, the coloring pigment is chosen from titanium dioxide, zirconium oxide, cerium oxide, zinc oxide, iron oxide, chromium oxide, manganese violet, ultramarine blue, chromium hydrate, ferric blue, aluminum powder, copper powder, silver powder, gold powder, barium sulfate, carbon black, pigments of D&C type, lakes, pearlescent pigments, and mixtures thereof.

The term "pearlescent pigments" should be understood as meaning iridescent particles of any shape, such as particles produced by certain shellfish in their shells or else synthesized.

The pearlescent agents can be chosen from white pearlescent agents, such as mica covered with titanium dioxide or with bismuth oxychloride; colored pearlescent agents, such as titanium oxide-coated mica covered with iron oxide, titanium oxide-coated mica covered with ferric blue or chromium oxide, or titanium oxide-coated mica covered with an organic pigment of the abovementioned type; and pearlescent agents based on bismuth oxychloride.

The composite pigment according to the present invention can provide a better feeling on use, because fine particles of coloring pigment(s), if used, can be firmly fixed on the small core particles so that it is possible to reduce free fine particles which have a high friction coefficient such that they do not easily spread on the skin and provide an unpleasant feeling on use.

The coloring pigment(s) may be used in the composite pigment according to the present invention in proportions such that the weight ratio of the small hollow core particle to the coloring pigment(s) is 50:50 to 90:10, preferably 50:50 to 80:20, and more preferably 50:50 to 70:30.

(Additional UV Filter)

As described above, the coating layer on the small hollow core particle may further comprise at least one additional UV filter. If two or more additional UV filters are used, they may be the same or different, preferably the same.

The additional UV filter used for the present invention may be active in the UV-A and/or UV-B region, preferably in the UV-A region or in the UV-A and UV-B region. The additional UV filter may be hydrophilic and/or lipophilic.

The additional UV filter may be solid or liquid. The terms "solid" and "liquid" mean solid and liquid, respectively, at 25° C. under 1 atm. The additional UV filter may be made from at least one organic or inorganic material, preferably at least one organic material.

The additional UV filter(s) may be selected from the group consisting of anthranilic derivatives; dibenzoylmethane derivatives; cinnamic derivatives; salicylic derivatives; camphor derivatives; benzophenone derivatives; β,β-diphenylacrylate derivatives; triazine derivatives; benzotriazole derivatives; benzalmalonate derivatives; benzimidazole derivatives; imidazoline derivatives; bis-benzoazolyl derivatives; p-aminobenzoic acid (PABA) and derivatives thereof; methylenebis(hydroxyphenylbenzotriazole) derivatives; benzoxazole derivatives; screening polymers and screening silicones; dimers derived from α-alkylstyrene; 4,4-diarylbutadienes; octocrylene and derivatives thereof, guaiazulene and derivatives thereof, rutin and derivatives thereof, flavonoids, biflavonoids, oryzanol and derivatives thereof, quinic acid and derivatives thereof, phenols, retinol, cysteine, aromatic amino acids, peptides having an aromatic amino acid residue, and mixtures thereof.

Mention may be made, as examples of the additional organic UV filter(s), of those denoted below under their INCI names, and mixtures thereof.

Anthranilic derivatives: Menthyl anthranilate, marketed under the trademark "Neo Heliopan MA" by Haarmann and Reimer.

Dibenzoylmethane derivatives: Butyl methoxydibenzoylmethane, marketed in particular under the trademark "Parsol 1789" by Hoffmann-La Roche; and isopropyl dibenzoylmethane.

Cinnamic derivatives: Ethylhexyl methoxycinnamate, marketed in particular under the trademark "Parsol MCX" by Hoffmann-La Roche; isopropyl methoxycinnamate; isopropoxy methoxycinnamate; isoamyl methoxycinnamate, marketed under the trademark "Neo Heliopan E 1000" by Haarmann and Reimer; cinoxate (2-ethoxyethyl-4-methoxy cinnamate); DEA methoxycinnamate; diisopropyl methylcinnamate; and glyceryl ethylhexanoate dimethoxycinnamate.

Salicylic derivatives: Homosalate (homomentyl salicylate), marketed under the trademark "Eusolex HMS" by Rona/EM Industries; ethylhexyl salicylate, marketed under the trademark "Neo Heliopan OS" by Haarmann and Reimer; glycol salicylate; butyloctyl salicylate; phenyl salicylate; dipropyleneglycol salicylate, marketed under the trademark "Dipsal" by Scher; and TEA salicylate, marketed under the trademark "Neo Heliopan TS" by Haarmann and Reimer.

Camphor derivatives, in particular, benzylidenecamphor derivatives: 3-benzylidene camphor, manufactured under the trademark "Mexoryl SD" by Chimex; 4-methylbenzylidene camphor, marketed under the trademark "Eusolex 6300" by Merck; benzylidene camphor sulfonic acid, manufactured under the trademark "Mexoryl SL" by Chimex; camphor benzalkonium methosulfate, manufactured under the trademark "Mexoryl SO" by Chimex; terephthalylidene dicamphor sulfonic acid, manufactured under the trademark "Mexoryl SX" by Chimex; and polyacrylamidomethyl benzylidene camphor, manufactured under the trademark "Mexoryl SW" by Chimex.

Benzophenone derivatives: Benzophenone-1 (2,4-dihydroxybenzophenone), marketed under the trademark "Uvinul 400" by BASF; benzophenone-2 (Tetrahydroxybenzophenone), marketed under the trademark "Uvinul D50" by BASF; Benzophenone-3 (2-hydroxy-4-methoxybenzophenone) or oxybenzone, marketed under the trademark "Uvinul M40" by BASF; benzophenone-4 (hydroxymethoxy benzophonene sulfonic acid), marketed under the trademark "Uvinul MS40" by BASF; benzophenone-5 (Sodium hydroxymethoxy benzophenone Sulfonate); benzophenone-6 (dihydroxy dimethoxy benzophenone); marketed under the trademark "Helisorb 11" by Norquay; benzophenone-8, marketed under the trademark "Spectra-Sorb UV-24" by American Cyanamid; benzophenone-9 (Disodium dihydroxy dimethoxy benzophenonedisulfonate), marketed under the trademark "Uvinul DS-49" by BASF; benzophenone-12, and n-hexyl 2-(4-diethylamino-2-hydroxybenzoyl)benzoate (UVINUL A+ by BASF).

β,β-Diphenylacrylate derivatives: Octocrylene, marketed in particular under the trademark "Uvinul N539" by BASF; and Etocrylene, marketed in particular under the trademark "Uvinul N35" by BASF.

Triazine derivatives: Diethylhexyl butamido triazone, marketed under the trademark "Uvasorb HEB" by Sigma 3V; 2,4,6-tris(dineopentyl 4'-aminobenzalmalonate)-s-triazine, bis-ethylhexyloxyphenol methoxyphenyl triazine marketed under the trademark <<TINOSORB S>> by CIBA GEIGY, and ethylhexyl triazone marketed under the trademark <<UVINUL T150>> by BASF.

Benzotriazole derivatives, in particular, phenylbenzotriazole derivatives: 2-(2H-benzotriazole-2-yl)-6-dodecyl-4-methylpheno, branched and linear; and those described in U.S. Pat. No. 5,240,975.

Methylene bis-benzotriazolyl tetramethylbutylphenol, such as 2,2'-methylenebis[6-(2H-benzotriazol-2-yl)-4-methyl-phenol] marketed in the solid form under the trademark "Mixxim BB/200" by Fairmount Chemical, or 2,2'-methylenebis[6-(2H-benzotriazol-2-yl)-4-(1,1,3,3-tetramethylbutyl)phenol] marketed in the micronized form in aqueous dispersion under the trademark "Tinosorb M" by BASF, or under the trademark "Mixxim BB/100" by Fairmount Chemical, and the derivatives as described in U.S. Pat. Nos. 5,237,071, 5,166,355, GB-2,303,549, DE-197,26,184 and EP-893,119, are in particular preferable.

Drometrizole trisiloxane, marketed under the trademark "Silatrizole" by Rhodia Chimie or "Mexoryl XL" by L'Oreal, as represented below.

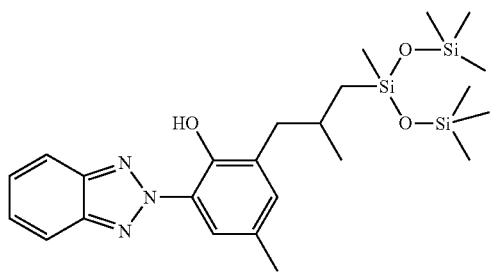 [SMILES: Cc1cc(CC(C)C[Si](C)(O[Si](C)(C)C)O[Si](C)(C)C)c(O)c(-n2nc3ccccc3n2)c1]

Benzalmalonate derivatives: Dineopentyl 4'-methoxybenzalmalonate, and polyorganosiloxane comprising benzalmalonate functional groups, such as polysilicone-15, marketed under the trademark "Parsol SLX" by Hoffmann-LaRoche.

Benzimidazole derivatives, in particular, phenylbenzimidazole derivatives: Phenylbenzimidazole sulfonic acid, marketed in particular under the trademark "Eusolex 232" by Merck, and disodium phenyl dibenzimidazole tetrasulfonate, marketed under the trademark "Neo Heliopan AP" by Haarmann and Reimer.

Imidazoline derivatives: Ethylhexyl dimethoxybenzylidene dioxoimidazoline propionate.

Bis-benzoazolyl derivatives: The derivatives as described in EP-669,323 and U.S. Pat. No. 2,463,264.

Para-aminobenzoic acid and derivatives thereof: PABA (p-aminobenzoic acid), ethyl PABA, Ethyl dihydroxypropyl PABA, pentyl dimethyl PABA, ethylhexyl dimethyl PABA, marketed in particular under the trademark "Escalol 507" by ISP, glyceryl PABA, and PEG-25 PABA, marketed under the trademark "Uvinul P25" by BASF.

Benzoxazole derivatives: 2,4-bis[5-1(dimethylpropyl) benzoxazol-2-yl-(4-phenyl)imino]-6-(2-ethylhexyl) imino-1,3,5-triazine, marketed under the trademark of Uvasorb K2A by Sigma 3V.

Screening polymers and screening silicones: The silicones described in WO 93/04665.

Dimers derived from α-alkylstyrene: The dimers described in DE-19855649.

4,4-Diarylbutadiene derivatives: 1,1-dicarboxy(2,2'-dimethylpropyl)-4,4-diphenylbutadiene.

Octocrylene and derivatives thereof: Octocrylene.

Quaiazulene and derivatives thereof: Guaiazulene and sodium guaiazulene sulfonate.

Rutin and derivatives thereof: Rutin and glucosylrutin.

Flavonoids: Robustin (isoflavonoid), genistein (flavonoid), tectochrysin (flavonoid), and hispidone (flavonoid).

Biflavonoids: Lanceolatin A, lanceolatin B, and hypnumbiflavonoid A.

Oryzanol and derivatives thereof: Γ-oryzanol.

Quinic acid and derivatives thereof: Quinic acid.

Phenols: Phenol.

Retinols: Retinol.

Cysteines: L-cysteine.

Peptides having an aromatic amino acid residue: Peptides having tryptophan, tyrosine or phenylalanine.

The preferred additional organic UV filter(s) is selected from:

butyl methoxydibenzoylmethane, ethylhexyl methoxycinnamate, homosalate, ethylhexyl salicylate, octocrylene, phenylbenzimidazole sulfonic acid, benzophenone-3, benzophenone-4, benzophenone-5, n-hexyl 2-(4-diethylamino-2-hydroxybenzoyl)benzoate, 4-methylbenzylidene camphor, terephthalylidene dicamphor sulfonic acid, disodium phenyl dibenzimidazole tetrasulfonate, ethylhexyl triazone, bis-ethylhexyloxyphenol methoxyphenyl triazine, diethylhexyl butamido triazone, 2,4,6-tris(dineopentyl 4'-aminobenzalmalonate)-s-triazine, 2,4,6-tris(diisobutyl 4'-aminobenzalmalonate)-s-triazine, 2,4,6-tris(biphenyl-4-yl)-1,3,5-triazine, 2,4,6-tris(terphenyl)-1,3,5-triazine, methylene bis-benzotriazolyl tetramethylbutylphenol, polysilicone-15, dineopentyl 4'-methoxybenzalmalonate, 1,1-dicarboxy(2,2'-dimethylpropyl)-4,4-diphenylbutadiene, 2,4-bis[5-1(dimethylpropyl)benzoxazol-2-yl-(4-phenyl)imino]-6-(2-ethylhexyl)imino-1,3,5-triazine, and their mixtures. A more preferable organic UV filter is butyl methoxydibenzoylmethane (Avobenzone).

The additional UV filter(s) may be used in the composite pigment according to the present invention in proportions such that the weight ratio of the small hollow core particle to the additional UV filter(s) is 50:50 to 90:10, preferably 50:50 to 80:20, and more preferably 50:50 to 70:30.

(Large Core Particle)

The large core particle to be used for the composite pigment according to the present invention is not limited, as long as the large core particle has a mean particle size or a mean particle diameter of 2 μm or more, preferably 3 μm or more, more preferably 4 μm or more, and even more preferably 5 μm or more. The mean particle size of the large core particle may be limited to 50 μm or less, preferably 30 μm or less, and more preferably 20 μm or less, and even more preferably 10 μm or less.

The mean particle size or mean particle diameter here is an arithmetic mean diameter, and can be determined, for example, by calculating the average of the dimensions of one hundred particles chosen on an image obtained with a scanning electron microscope.

The large core particle may be hollow or solid. It may be preferable to use solid large particle.

The large particle can be in any shape. For example, it is possible to use a large particle in the form of a plate with an aspect ratio of at least 5, preferably more than 10, more preferably more than 20, and more preferably more than 50.

The aspect ratio can be determined by the average thickness and the average length according to the formula: aspect ratio=length/thickness.

If a plate-like particle is used for the present invention, it is preferable that the plate-like particle has a length ranging 2 μm or more, preferably 3 μm or more, more preferably 4 μm or more, and even more preferably 5 μm or more, but ranging 50 μm or less, preferably 30 μm or less, and more preferably 20 μm or less, and even more preferably 10 μm or less.

In a preferred embodiment, the large core particle has a spherical shape.

The material of the large core particle is not limited. The material can be at least one inorganic material and/or at least one organic material, preferably at least one organic material.

The inorganic material and/or organic material may be hollow or porous. The porosity of the material may be characterized by a specific surface area of from 0.05 $m^2/g$ to 1,500 $m^2/g$, more preferably from 0.1 $m^2/g$ to 1,000 $m^2/g$, and more preferably from 0.2 $m^2/g$ to 500 $m^2/g$ according to the BET method.

Preferably, the inorganic material can be selected from the group consisting of mica, synthetic mica, talc, sericite, boron nitride, glass flakes, calcium carbonate, barium sulfate, titanium oxide, hydroxyapatite, silica, silicate, zinc oxide, magnesium sulfate, magnesium carbonate, magnesium trisilicate, aluminum oxide, aluminum silicate, calcium silicate, calcium phosphate, magnesium oxide, bismuth oxychloride, kaolin, hydrotalcite, mineral clay, synthetic clay, iron oxide, and mixtures thereof. Natural mica, synthetic mica, sericite, kaolin, talc, silica and mixtures thereof are more preferable.

In particular, silica particles such as P-1500 marketed by JGC C&C are preferable as inorganic large particles.

Preferably, the organic material can be selected from the group consisting of poly(meth)acrylates, polyamides, silicones, polyurethanes, polyethylenes, polypropylenes, polystyrenes, copolystyrenes, polyhydroxyalkanoates, polycaprolactams, poly(butylene)succinates, polysaccharides, polypeptides, polyvinyl alcohols, polyvinyl resins, fluoropolymers, waxes, amidosulfonic acid polyvalent metal salts, acylated amino acids, and mixtures thereof. As the fluoropolymers, for example, PTFE may be used. As the amidosulfonic acid polyvalent metal salts, for example, N-lauroyltaurine calcium may be used. As the acylated amino acids, lauroyllysine may be used. Polyamides such as Nylon®, polyhydroxyalkanoates such as polylactic acids, poly(meth)acrylates such as polymethylmethacrylates, silicones, fluoropolymers, and mixtures thereof are more preferable.

In particular, polymethylmethacrylate particles such as MR-7GC marketed by Soken in Japan, polyamide particles such as SP-500 marketed by Toray, Orgasol marketed by Arkema, and PTFE particles such as Ceridust 9205F marketed by Clariant, are preferable as organic large core particles.

The large core particle may or may not be coated beforehand. In a particular embodiment, the large core particle is originally coated. The material of an original coating of the large core particle is not limited, but an organic material such as an amino acid, an N-acylamino acid, an amido, a silicone, a modified silicone and a polyolefin, is preferable. As the organic material, mention may be made of lauroyl lysine, acryl-modified silicone and polyethylene.

In particular, silica particles coated with polyethylene such as ACEMATT OK412 marketed by Degussa may be preferable as coated (inorganic) large particles.

In the composite pigment according to the present invention, the weight ratio of the small hollow core particle(s) to the large core particle(s) may be 10:90 to 90:10, preferably 20:80 to 80:20, and more preferably 30:70 to 70:30.

In a particular embodiment, the weight ratio of the small hollow core particle(s)/the large core particle(s)/the inorganic solid UV filter(s) may be 20:50:30 to 50:20:30, preferably 35:15:50 to 15:35:50, and more preferably 10:20:70 to 20:10:70.

In a preferred embodiment, the weight ratio of the small hollow core particle(s)/the large core particle(s)/the inorganic solid UV filter(s) may be 50:20:30 or 35:15:50.

In a preferred embodiment, the composite pigment according to the present invention may satisfy the following requirements:

the small hollow core particle comprises at least one copolystyrene, preferably styrene/acrylate copolymer and/or cross-linked styrene/methyl methacrylate copolymer;

the large core particle comprises at least one poly(meth)acrylate, preferably methyl methacrylate polymer; and the small hollow core and large core particles are at least in part covered with at least one coating layer comprising metal oxide, preferably titanium oxide.

(Method for Preparing Composite Pigment)

The composite pigment according to the present invention can be prepared by subjecting at least one small hollow core particle with a mean particle size more than 100 nm and of less than 1 μm, preferably less than 600 nm, and more preferably less than 400 nm wherein the small hollow core particle comprises at least one organic polymer;

optionally at least one large core particle with a mean particle size of 2 μm or more, preferably 3 μm or more, more preferably 4 μm or more, and even more preferably 5 μm or more;

at least one inorganic solid UV filter; and optionally at least one coloring pigment and/or at least one additional UV filter to a mechanochemical fusion process.

The small core particle, the large core particle, the inorganic solid UV filter, the coloring pigment, and the additional UV filter are as explained above.

Mechanochemical fusion process means a process in which mechanical power such as impact force, friction force or shear force is applied to a plurality of subjects to cause fusion between the subjects.

The mechanochemical fusion process may be performed by, for example, an apparatus comprising a rotating chamber and a fixed inner piece with a scraper, such as a mechanofusion system marketed by Hosokawa Micron Corporation in Japan.

It is preferable to use a hybridizer process as the mechanochemical fusion process.

The hybridizer process was developed in the 1980s. The hybridizer process is a class of mechanochemical fusion processes in which strong mechanical power is applied to a plurality of particles to cause a mechanochemical reaction to form a composite particle.

According to the hybridizer process, the mechanical power is imparted by a high speed rotor which can have a diameter from 10 cm to 1 m, and can rotate at a speed of 1,000 rpm to 100,000 rpm. Therefore, the hybridizer process can be defined as a mechanochemical fusion process using such a high speed rotor. The hybridizer process is performed in air or under dry conditions. Thus, due to the high speed rotation of the rotor, high speed air flow may be generated near the rotor. However, some liquid materials may be subjected to the hybridizer process together with solid materials. The term "hybridizer process" has been used as a technical term.

The hybridizer process can be performed by using a hybridization system marketed by, for example, Nara Machinery in Japan, in which at least two types of particles, typically core particles and fine particles, are fed into a hybridizer equipped with a high speed rotor having a plurality of blades in a chamber under dry conditions, and the particles are dispersed in the chamber and mechanical and thermal energy (e.g., compression, friction and shear stress) are imparted to the particles for a relatively short period of time such as 1 to 10 minutes, preferably 1 to 5 minutes. As a result, one type of particles (e.g., fine particles) is embedded or fixed on the other type of particles (e.g., core particle) to form composite particles. It is preferable that the particles have been subjected to electrostatic treatment(s) such as shaking to form an "ordered mixture" in which one type of particles is spread to cover the other type of particles. The hybridizer process can also be performed by using a theta composer marketed by Tokuju Corporation in Japan.

The hybridizer process can also be performed by using a Composi Hybrid or a Mechano Hybrid marketed by Nippon coke.

According to one embodiment of the present invention, for example, small hollow core particles, large core particles and inorganic solid UV filter(s) as well as optionally additional material(s) such as coloring pigment(s) and/or additional UV filter(s) if necessary, can be fed into such a hybridizer to form a composite pigment. The hybridizer process can be performed by using a rotor rotating at about 8,000 rpm (100 msec) for about 3 minutes.

According to one embodiment of the present invention, the small hollow core particle(s) and the large core particle(s) can be used in proportions such that the weight ratio of the small hollow core particle(s) to the large core particle(s) is 10:90 to 90:10, preferably 20:80 to 80:20, and more preferably 30:70 to 70:30.

In a particular embodiment, the weight ratio of the small hollow core particle(s)/the large core particle(s)/the inorganic solid UV filter(s) may be 20:50:30 to 50:20:30, preferably 35:15:50 to 15:35:50, and more preferably 10:20:70 to 20:10:70.

In a preferred embodiment, the weight ratio of the small hollow core particle(s)/the large core particle(s)/the inorganic solid UV filter(s) may be 50:20:30 or 35:15:50.

The mechanochemical fusion process, in particular the hybridizer process, enables to provide a composite pigment in which small hollow core particles are at least in part covered by at least one layer comprising at least one inorganic solid UV filter, and optionally at least one coloring pigment and/or at least one additional UV filter wherein the small core particle comprises at least one organic polymer. If large core particles are used, the surface of the large core particles may also be at least in part covered by at least one layer comprising at least one inorganic solid UV filter, and optionally at least one coloring pigment and/or at least one additional UV filter.

Furthermore, the mechanochemical fusion process, in particular the hybridizer process, can provide ordered array (e.g., uniform coverage) of inorganic solid UV filter(s), and optionally at least one coloring pigment and/or at least one additional UV filter on small hollow core particles and provides strong bonds at the surface of the small core particle and a coating layer comprising the inorganic solid UV filter(s), and optionally coloring pigment(s) and/or additional UV filter(s).

If the large core particles are used in combination with the small core particles, according to the present invention, the inorganic solid UV filter, and optionally the additional UV filter and/or the coloring pigment, can be effectively bound on the surface of the small hollow core particles due to the anchor effects by the collision of the large core particles to the small hollow core particles. Therefore, the UV filtering effects, and optionally coloring effects, can be further enhanced.

It should be noted that the mechanochemical fusion process, in particular the hybridizer process, is quite different from other processes using, for example, a beads mill and a jet mill. In fact, a beads mill causes pulverization or aggregation of core particles, and a jet mill causes pulverization of core particles and uniform coating of a core particle by fine particles is difficult to be formed.

If necessary, an additional process for further coating the composite pigments with UV filter(s) and/or coloring material(s) may be performed. As a result of this additional process, the composite pigment according to the present invention may be coated with a further layer comprising UV filter(s) and/or coloring material(s), preferably consisting of UV filter(s) and/or coloring material(s).

(Cosmetic Composition)

The composite pigment, as described above, according to the present invention can be present in the cosmetic composition according to the present invention in an amount ranging from 0.01% to 99% by weight, preferably from 0.1% to 50% by weight, and more preferably from 1% to 30% by weight, relative to the total weight of the composition.

Preferably, the composite pigment according to the present invention can be used in cosmetic compositions to be applied to keratin substances such as skin, hair, and nails, providing superior UV shielding effects, and optionally coloring effects, because the composite pigment can exhibit good UV filtering effects possibly with a transparent or clear appearance and/or good coloring effects such as more transparent or clearer and more bright coloring, without the risk of affecting keratin substances.

Since the composite pigment according to the present invention can reduce free particles which have a high friction coefficient such that they do not easily spread on the skin and provide an unpleasant feeling on use, the cosmetic composition according to the present invention has reduced friction, and therefore, can provide the effect of a better feeling on use.

The cosmetic composition according to the present invention may further comprise at least one filler and/or at least one oil.

As used herein, the term "filler" should be understood as meaning colorless natural or synthetic particles of any shape which are insoluble in the medium of the composition, whatever the temperature at which the composition is manufactured. Thus, the filler is different from the coloring pigment as described above.

The fillers may be inorganic or organic and of any shape (for instance, platelet, spherical, and oblong shapes) and with any crystallographic form (for example, sheet, cubic, hexagonal, orthorhombic, and the like). Examples of suitable additional fillers include, but are not limited to, talc; mica; silica; kaolin; powders of polyamide such as Nylon®; poly-β-3-alanine powders; polyethylene powders; polyurethane powders, such as the powder formed of hexamethylene diisocyanate and trimethylol hexyllactone copolymer sold under the name Plastic Powder D-400 by Toshiki; the powders formed of tetrafluoroethylene polymers (Teflon®);

lauroyllysine; starch; boron nitride; polymeric hollow microspheres, such as microspheres of poly(vinylidene chloride)/acrylonitrile, for example Expancel® (Nobel Industrie), and microspheres of acrylic acid copolymers; silicone resin powders, for example, silsesquioxane powders (for instance, silicone resin powders disclosed in European Patent No. 0 293 795 and Tospearls® from Toshiba); poly (methyl methacrylate) particles; precipitated calcium carbonate; magnesium carbonate; basic magnesium carbonate; hydroxyapatite; hollow silica microspheres; glass microcapsules; ceramic microcapsules; metal soaps derived from organic carboxylic acids comprising from 8 to 22 carbon atoms, for example, from 12 to 18 carbon atoms, such as zinc stearate, magnesium stearate, lithium stearate, zinc laurate, and magnesium myristate; barium sulphate; and mixtures thereof.

The filler may be present in the composition in an amount ranging from 0.1% to 80% by weight, with respect to the total weight of the composition, for example, from 1% to 25% by weight, or from 3% to 15% by weight.

The term "oil" is understood to mean a fatty substance which is liquid at ambient temperature (25° C.).

Use may be made, as oils which can be used in the composition of the invention, for example, of hydrocarbon oils of animal origin, such as perhydrosqualene (or squalane); hydrocarbon oils of vegetable origin, such as triglycerides of caprylic/capric acids, for example those marketed by Stearineries Dubois or those marketed under the trademarks Miglyol 810, 812 and 818 by Dynamit Nobel, or oils of vegetable origin, for example sunflower, maize, soybean, cucumber, grape seed, sesame, hazelnut, apricot, macadamia, arara, coriander, castor, avocado or jojoba oil or shea butter oil; synthetic oils; silicone oils, such as volatile or non-volatile polymethylsiloxanes (PDMSs) comprising a linear or cyclic silicone chain which are liquid or paste at ambient temperature; fluorinated oils, such as those which are partially hydrocarbon and/or silicone, for example those described in JP-A-2-295912; ethers, such as dicaprylyl ether (CTFA name); and esters, such as benzoate $C_{12}$-$C_{15}$ fatty alcohols (Finsolv TN from Finetex); arylalkyl benzoate derivatives, such as 2-phenylethyl benzoate (X-Tend 226 from ISP); amidated oils, such as isopropyl N-lauroylsarcosinate (Eldew SL-205 from Ajinomoto), and their mixtures.

The oily phase can also comprise one or more fatty substances selected, for example, from fatty alcohols (cetyl alcohol, stearyl alcohol, cetearyl alcohol), fatty acids (stearic acid) or waxes (paraffin wax, polyethylene waxes, carnauba wax, beeswax). The oily phase can comprise lipophilic gelling agents, surfactants or also organic or inorganic particles.

The oily phase can preferably represent from 1 to 70% of oil by weight, with respect to the total weight of the composition.

The composition according to the present invention may further comprise at least one additional conventional cosmetic ingredient which may be chosen, for example, from hydrophilic or lipophilic gelling and/or thickening agents, surfactants, antioxidants, fragrances, preservatives, neutralizing agents, sunscreens, vitamins, moisturizing agents, self-tanning compounds, antiwrinkle active agents, emollients, hydrophilic or lipophilic active agents, agents for combating pollution and/or free radicals, sequestering agents, film-forming agents, dermo-decontracting active agents, soothing agents, agents which stimulate the synthesis of dermal or epidermal macromolecules and/or which prevent their decomposition, antiglycation agents, agents which combat irritation, desquamating agents, depigmenting agents, antipigmenting agents, propigmenting agents, NO-synthase inhibitors, agents which stimulate the proliferation of fibroblasts and/or keratinocytes and/or the differentiation of keratinocytes, agents which act on microcirculation, agents which act on energy metabolism of the cells, healing agents, and mixtures thereof.

The composition according to the present invention may be in various forms, for example, suspensions, dispersions, solutions, gels, emulsions, such as oil-in-water (O/W), water-in-oil (W/O), and multiple (e.g., W/O/W, polyol/O/W, and O/W/O) emulsions, creams, foams, sticks, dispersions of vesicles, for instance, of ionic and/or nonionic lipids, two-phase and multi-phase lotions, sprays, powders, and pastes. The composition may be anhydrous, for example, it can be an anhydrous paste or stick. The composition may also be a leave-in composition.

According to one embodiment, the cosmetic composition according to the present invention may be in the form of a powdery composition or a liquid or solid composition, such as an oily-solid cosmetic composition or an anhydrous composition.

In particular, the powdery cosmetic composition according to the present invention can have reduced friction which provides a smooth feeling to use, and can have good compactability which provides high stability against physical impact, due to the inclusion of the composite pigment according to the present invention.

Furthermore, the powdery cosmetic composition according to the present invention can show preferable cosmetic effects such as good fitting to the skin, homogeneous appearance, hiding the color of the skin, hiding the pores and lines on the skin, making the pores and lines on the skin less remarkable, and matt appearance, due to the inclusion of the composite pigment according to the present invention.

On the other hand, the liquid cosmetic composition according to the present invention can show good visual optical effects such as matt and haze effects, due to the inclusion of the composite pigment according to the present invention.

In any event, the powdery and liquid cosmetic composition according to the present invention has better UV filtering effects, and optionally better coloring effects, in addition to reduce the risk of fine particles of inorganic solid UV filter(s) and optional coloring pigment(s) penetrating into the skin via pores on the skin.

According to another embodiment, the cosmetic composition according to the present invention may be in the form of, for example, a compact powder, a lotion, a serum, a milk, a cream, a base foundation, an undercoat, a make-up base coat, a foundation, a face powder, cheek rouge, a lipstick, a lip cream, an eye shadow, an eyeliner, a loose powder, a concealer, a nail coat, mascara, a sunscreen and the like.

According to another embodiment, the cosmetic composition according to the present invention may be in the form of a foam.

According to this embodiment, the cosmetic composition according to the present invention can be packaged in a foam dispenser. It can involve either products referred to as "aerosols" dispensed from a pressurized container by means of a propellant gas and thus forming a foam at the time of their dispensing, or products dispensed from a container by means of a mechanical pump connected to a dispensing head where the passage of the cosmetic composition through the dispensing head transforms it into a foam in the area of the outlet orifice of such a head at the latest.

According to a first variant, the dispenser can be an aerosol furthermore containing the cosmetic composition according to the present invention; and a propellant gas. For the purposes of the invention, the term "propellant" means any compound that is gaseous at a temperature of 20° C. and at atmospheric pressure, and that can be stored under pressure in liquid or gaseous form in an aerosol container. The propellant may be chosen from optionally halogenated volatile hydrocarbons, such as n-butane, propane, isobutane, pentane or a halogenated hydrocarbon, and mixtures thereof. Carbon dioxide, nitrous oxide, dimethyl ether (DME), nitrogen or compressed air may also be used as propellant. Mixtures of propellants may also be used. Dimethyl ether and/or non-halogenated volatile hydrocarbons are preferably used.

The propellant gas which can be used may be chosen among the previously mentioned gases and in particular among carbon dioxide, nitrogen, nitrogen oxide, dimethyl ether, volatile hydrocarbons such as butane, isobutane, propane and pentane, and mixtures thereof.

According to another variant, the cosmetic composition according to the present invention can be in a "pump bottle" type foam dispenser. These dispensers include a dispensing head for delivering the cosmetic composition, a pump and a plunger tube for transferring the cosmetic composition from the container, into the head, for dispensing the product. The foam is formed by forcing the cosmetic composition to pass through a material including a porous substance such as a sintered material, a filtering grid of plastic or metal, or similar structures.

Such dispensers are known to a person skilled in the art and are described in the patents: U.S. Pat. No. 3,709,437 (Wright), U.S. Pat. No. 3,937,364 (Wright), U.S. Pat. No. 4,022,351 (Wright), U.S. Pat. No. 4,1147,306 (Bennett), U.S. Pat. No. 4,184,615 (Wright), U.S. Pat. No. 4,598,862 (Rice), U.S. Pat. No. 4,615,467 (Grogan et al.), and U.S. Pat. No. 5,364,031 (Tamiguchi et al.).

It is to be understood that a person skilled in the art can choose the appropriate presentation form, as well as its method of preparation, on the basis of his/her general knowledge, taking into account the nature of the constituents used, for example, their solubility in the vehicle, and the application envisaged for the composition.

EXAMPLES

The present invention will be described in more detail by way of examples, which however should not be construed as limiting the scope of the present invention.

Examples 1 and 2, and Comparative Examples 1 to 3

The components shown in Table 1 were subjected to a hybridizer process using a Hybridizer equipped with a high-speed rotor having a plurality of blades in a chamber in dry conditions, marketed by Nara Machinery Co., Ltd. in Japan, to obtain a composite pigment according to Examples 1 and 2, as well as Comparative Example 1.

In detail, for each of Examples 1 and 2, and Comparative Example 1, the components shown in Table 1 were mixed at the mixing ratio (the numerals in Table 1 are based on parts by weight) shown in Table 1 in a plastic bag by hand shaking for a short period of time. The mixture was put in the Hybridizer, and the rotor was revolved at 8,000 rpm (100 m/s linear velocity) for 3 minutes to obtain the composite pigments according to Examples 1 and 2, and Comparative Example 1.

As Comparative Example 2, a marketed composite pigment with silica and titanium dioxide (SUNSIL-T™50 marketed by Sunjin Chemical Co., Ltd.) was used. In this composite pigment, titanium oxide fine particles are distributed in a solid silica particle. The particle size of the composite pigment according to Comparative Example 2 was 4 μm.

As Comparative Example 3, a marketed composite pigment with silica and titanium dioxide (STM ACS-0050510 marketed by JGC Catalysts and Chemicals Ltd.) was used. In this composite pigment, titanium oxide fine particles are distributed in a coating on a solid silica particle. The particle size of the composite pigment according to Comparative Example 3 was 0.5 μm.

In Table 1, the amount of titanium oxide in each composite pigment is shown in the column of "Ratio (wt %)" as a weight ratio relative to the total weight of the composite pigment.

[UV Absorbance Evaluation]

Absorbance of UV waves of each of the composite pigments according to Examples 1 and 2, and each of Comparative Examples 1 to 3, was measured by use of a UV/VIS spectrophotometer type V-550 (JASCO, Japan) as follows.

A solvent was prepared by mixing isododecane and polyhydroxystearic acid such that the concentration of polyhydroxystearic acid was 3 wt %.

Each of the composite pigments according to Examples 1 and 2, as well as Comparative Examples 1 to 3 was dispersed in the above solvent by using ultrasonic waves for 1 minute to obtain a sample, such that the concentration of the composite pigment in the sample was 0.1 wt %. If agglomerates were still present, the ultrasonic treatment was repeated.

The obtained sample was put into a quartz cell having a 2 mm light pathway. The UV absorbance of the sample in the wavelength of from 280 to 400 nm was measured by use of a UV/VIS spectrophotometer type V-550 (JASCO, Japan).

The results are shown in Table 1 in the column of "UV*".

It is clear that the UV absorbance of the composite pigments according to Examples 1 and 2 is enhanced.

Since a relatively large amount of $TiO_2$ is used in Example 1, the UV absorbance value of Example 1 is higher than that of Example 2. Since $TiO_2$ nano particles easily form aggregations which are difficult to show good UV absorption, it is surprising to observe that a relatively large amount of $TiO_2$ can exert higher UV absorbance for the composite pigment according to Example 1.

Since Comparative Example 1 uses a solid small core, the UV absorbance of the composite pigment according to Comparative Example 1 is smaller than that of the composite pigment according to Example 1 or 2.

[SEM/TEM Observations]

The composite pigments according to Examples 1 and 2 were observed by using SEM (Scanning Electron Microscope)/TEM (Transmission Electron Microscope). It was found that almost all the surface of the small hollow particle was covered with nano particles of $TiO_2$, and that a part of the large particle was covered with nano particles of $TiO_2$.

TABLE 1

| | Small Hollow Core Styrene/Acrylate Copolymer | Small Solid Core PMMA(1) | Large Core PMMA(2) | Large Core Nylon 12 | UV Filter TiO$_2$ | Ratio (wt %) | UV* |
|---|---|---|---|---|---|---|---|
| Particle Size | 350 nm | 350 nm | 6 μm | 5 μm | 15 nm | 24.9 | |
| Ex. 1 | 35 | — | 15 | — | 50 | 41.5 | 129 |
| Ex. 2 | 50 | — | 20 | — | 30 | 24.9 | 102 |
| Comp. Ex. 1 | — | 50 | — | 20 | 30 | 24.9 | 91 |
| Comp. Ex. 2 | — | — | — | — | — | 43.5 | 19 |
| Comp. Ex. 3 | — | — | — | — | — | 5.0 | 5 |

Syrene/Acrylate Copolymer: Sunspheres marketed by Rohm and Haas
PMMA(1): MP-2200 marketed by Soken in Japan
PMMA(2): MR-7GC marketed by Soken in Japan
Nylon 12: SP-500 marketed by Toray in Japan
TiO$_2$: MT-100 TV marketed by Tayca in Japan
UV*: UV absorbance in the wavelength region from 280 to 400 nm Examples 3 and 4, and Comparative Examples 4 to 6

A sun-care formulation in the form of an O/W emulsion was prepared by mixing the components shown in Table 2. The numerals shown in Table 2 are based on percent by weight relative to the total weight of the formulation.

[In Vitro SPF Value Evaluation]

Each of the sun-care formulations according to Examples 3 and 4, and Comparative Examples 4 to 6 was applied onto

TABLE 2

| Phase | Components | Ex. 3 | Ex. 4 | Comp. Ex. 4 | Comp. Ex. 5 | Comp. Ex. 6 |
|---|---|---|---|---|---|---|
| A | Water | 35 | 35 | 35 | 35 | 35 |
| | Methylparaben | 0.4 | 0.4 | 0.4 | 0.4 | 0.4 |
| | Glycerin | 6 | 6 | 6 | 6 | 6 |
| | Propyleneglycol | 6 | 6 | 6 | 6 | 6 |
| | Terephthalidene Dicamphor Sulfinic Acid (MEXORYL SX) | 4.5 | 4.5 | 4.5 | 4.5 | 4.5 |
| | Triethanolamine | 0.16 | 0.16 | 0.16 | 0.16 | 0.16 |
| | Disodium EDTA potassium | 0.1 | 0.1 | 0.1 | 0.1 | 0.1 |
| | Cetyl phosphate | 1 | 1 | 1 | 1 | 1 |
| B1 | C$_{12-15}$ Alkyl benzoate | 7.5 | 7.5 | 7.5 | 7.5 | 7.5 |
| | Bis-Ethylhexyloxyphenol Methoxyphenyl Triazine (<<TINOSORB S>> by BASF) | 2 | 2 | 2 | 2 | 2 |
| | n-Hexyl 2-(4-diethylamino-2-hydroxybenzoyl)benzoate ("UVINULA+" by BASF) | 4 | 4 | 4 | 4 | 4 |
| | Ethylhexyl Triazone ("UVINUL T150" by BASF) | 2 | 2 | 2 | 2 | 2 |
| B2 | Stearic acid | 1 | 1 | 1 | 1 | 1 |
| | Triethanolamine | 0.3 | 0.3 | 0.3 | 0.3 | 0.3 |
| | Glyceryl stearate (and) PEG-100 staerate | 1 | 1 | 1 | 1 | 1 |
| | Dimethicone | 0.5 | 0.5 | 0.5 | 0.5 | 0.5 |
| | Ethylparaben | 0.3 | 0.3 | 0.3 | 0.3 | 0.3 |
| | Tocopherol | 0.1 | 0.1 | 0.1 | 0.1 | 0.1 |
| | Phenoxyethanol | 0.7 | 0.7 | 0.7 | 0.7 | 0.7 |
| B3 | Composite pigment according to Example 1 | 10 | — | — | — | — |
| | Composite pigment according to Example 2 | — | 5 | — | — | — |
| | Composite pigment according to Comp. Example 1 | — | — | — | — | 10 |
| | Styrene/Acrylate Copolymer | — | — | 5 | 1.75 | |
| | PMMA | — | — | 2 | 0.75 | |
| | Titanium dioxide (and) aluminum hydroxide (and) stearic acid | — | — | 3 | 2.5 | — |
| C | Isohexadecane | 4.5 | 4.5 | 4.5 | 4.5 | 4.5 |
| | Acrylates/C$_{10-30}$ alkyl acrylate crosspolymer | 0.25 | 0.25 | 0.25 | 0.25 | 0.25 |
| | Xanthan gum | 0.1 | 0.1 | 0.1 | 0.1 | 0.1 |
| D | Water | 1 | 1 | 1 | 1 | 1 |
| | Triethanolamine | 0.25 | 0.25 | 0.25 | 0.25 | 0.25 |
| E | Water | 9.34 | 14.34 | 9.34 | 14.34 | 19.34 |
| G | Alcohol (denat.) | 2 | 2 | 2 | 2 | 2 |
| | SPF | 122 | 85 | 80 | 68 | 7 | a PMMA plate in an amount of 0.75 mg/cm², and the SPF value of the make-up base sample was measured by an SPF analyzer UV-2000S. The results are shown in Table 2.

The result of Example 3 should be compared with that of Comparative Example 4, because Comparative Example 4 includes a simple mixture of the small hollow particle, the large particle and TiO₂, whereas they were hybridized in the composite pigment included in the sun-care formulation according to Example 3. It is clear that the SPF value (122) in Example 3 is much higher than that (80) in Comparative Example 4.

The result of Example 4 should be compared with that of Comparative Example 5, because Comparative Example 5 includes a simple mixture of the small hollow particle, the large particle and TiO₂, whereas they were hybridized in the composite pigment included in the sun-care formulation according to Example 4. It is clear that the SPF value (85) in Example 4 is much higher than that (68) in Comparative Example 5.

Comparative Example 6 functions as a control.

Next, some examples of the formulation of the cosmetic composition according to the present invention are shown below.

Example 5

Cosmetic Milk

TABLE 3

| INGREDIENTS | Wt % |
| --- | --- |
| BUTYL METHOXYDIBENZOYLMETHANE | 1.5 |
| TEREPHTHALYLIDENE DICAMPHOR SULFONIC ACID | 0.9 |
| OCTOCRYLENE | 5 |
| STEARIC ACID | 1 |
| GLYCERYL STEARATE (and) PEG-100 STEARATE | 1 |
| POTASSIUM CETYL PHOSPHATE | 1 |
| COMPOSITE PIGMENT ACCORDING TO EXAMPLE 2 | 8 |
| NYLON-12 | 2.5 |
| ISOHEXADECANE | 4.5 |
| XANTHAN GUM | 0.1 |
| ACRYLATES/C10-30 ALKYL ACRYLATE CROSSPOLYMER | 0.25 |
| ZEA MAYS (CORN) STARCH | 2 |
| SYNTHETIC WAX | 1 |
| DIMETHICONE | 0.5 |
| ALCOHOL DENAT. | 2 |
| WATER | qsp 100 |
| $C_{12-15}$ ALKYL BENZOATE | 7.5 |
| GLYCERIN | 6 |
| PROPYLENE GLYCOL | 6 |
| PHENOXYETHANOL | 0.7 |
| ETHYLPARABEN | 0.3 |
| METHYLPARABEN | 0.2 |
| Total | 100 |

Example 6

Serum

TABLE 4

| INGREDIENTS | Wt % |
| --- | --- |
| STEARIC ACID | 0.1 |
| POTASSIUM CETYL PHOSPHATE | 0.05 |
| SUCROSE STEARATE | 3 |
| COMPOSITE PIGMENT ACCORDING TO EXAMPLE 1 | 15 |
| VINYL DIMETHICONE/METHICONE SILSESQUIOXANE CROSSPOLYMER | 2 |
| BORON NITRIDE | 1 |
| SILICA | 1 |
| CAPRYLIC/CAPRIC TRIGLYCERIDE | 4.5 |
| HYDROGENATED LECIHIN | 0.3 |
| DICAPRYLYL CARBONATE | 2 |
| XANTHAN GUM | 0.25 |
| CARBOMER | 0.2 |
| ACRYLATES/$C_{10-30}$ ALKYL ACRYLATE CROSSPOLYMER | 0.1 |
| ALCOHOL DENAT. | 3 |
| WATER | qsp 100 |
| GLYCERIN | 7 |
| CAPRYLYL GLYCOL | 0.3 |
| SALICYLIC ACID | 0.2 |
| PHENOXYETHANOL | 0.3 |
| Total | 100 |

Examples 7 and 8

Cream

TABLE 5

| Phase | INGREDIENTS | Ex. 7 (wt %) | Ex. 8 (wt %) |
| --- | --- | --- | --- |
| A | GLYCERIN | 5 | 5 |
| | EDTA | 0.1 | 0.1 |
| | POTASSIUM CETYL PHOSPHATE (AMPHISOL K) | 1 | 1 |
| | TEREPHTHALYLIDENE DICAMPHOR SULFONIC ACID (MEXORYL SX) | 1 (AM) | 1 (AM) |
| | DEIONIZED WATER | qsp 100 | qsp 100 |
| | TRIETHANOLAMINE | 0.3 | 0.3 |
| | PRESERVATIVES | 1.2 | 1.2 |
| B1 | $C_{12-15}$ ALKYL BENZOATE (TEGOSOFT TN) | 20 | 20 |
| | PRESERVATIVES | 0.25 | 0.25 |
| | STEARIC ACID | 1.5 | 1.5 |
| | GLYCERYL STEARATE (and) PEG-100 STEARATE | 1 | 1 |
| | CETYL ALCOHOL | 0.5 | 0.5 |
| | STEARYL ALCOHOL and STEARYL GLUCOSIDE | 2 | 2 |
| | POLY DIMETHYLSILOXANE (350 cst) | 0.5 | 0.5 |
| | TRIETHANOLAMINE | 0.45 | 0.45 |
| | BUTYLMETHOXYDIBENZOYLMETHANE (PARSOL 1789-DSM) | 4 | 4 |

TABLE 5-continued

| Phase | INGREDIENTS | Ex. 7 (wt %) | Ex. 8 (wt %) |
|---|---|---|---|
| | COMPOSITE PIGMENT ACCORDING TO EXAMPLE 2 | 4 | — |
| | COMPOSITE PIGMENT ACCORDING TO EXAMPLE 1 | — | 8 |
| | DROMETRIZOLE TRISILOXANE (MEXORYL XL) | 3 | 3 |
| | 2-ETHYLHEXYL α-CYANO-β,β'-DIPHENYLACRYLATE | 5 | 5 |
| | ETHYLHEXYL TRIAZONE (UVINUL T150) | 1 | 1 |
| | TITANIUM DIOXIDE (AND) ALUMINUM HYDROXIDE (AND) STEARIC ACID (MT TV) | 5 | 5 |
| B2 | ISOHEXADECANE | 1 | 1 |
| | ACRYLATES/C$_{10-30}$ ALKYL ACRYLATE CROSSPOLYMER | 0.2 | 0.2 |
| | XANTHAN GUM | 0.2 | 0.2 |
| | CYCLOPENTADIMETHYLSILOXANE | 5 | 5 |
| Total | | 100 | 100 |

AM: Active Material

Example 9

Powder Foundation

TABLE 6

| Phase | Components | Wt % |
|---|---|---|
| A | Talc | 39.8 |
| | Sericite | 25 |
| | Mica | 5 |
| | Zinc Stearate/Zinc Oxide | 1 |
| B1 | Titanium Oxide | 8 |
| | Composite Pigment according to Example 1 | 10 |
| B2 | Iron Oxide (Red) | 0.5 |
| | Iron Oxide (Yellow) | 1.5 |
| | Iron Oxide (Blue) | 0.2 |
| D | Mineral Oil/Paraffin Liquid | 4 |
| | Phenyltrimethicone | 4.5 |
| | Phenoxyethanol | 0.5 |
| Total | | 100 |

Example 10

Loose Powder

TABLE 7

| Ingredients | Wt % |
|---|---|
| TALC | 65.85 |
| MICA | 10.00 |
| ALUMINUM STARCH OCTENYLSUCCINATE | 10.00 |
| COMPOSITE PIGMENT ACCORDING TO EXAMPLE 2 | 10.00 |
| IRON OXIDES (and) ISOPROPYL TITANIUM TRIISOSTEARATE | 0.15 |
| MAGNESIUM STEARATE | 2.00 |
| ISOCETYL STEARATE | 1.00 |
| DIMETHICONE | 1.00 |
| Total | 100 |

Example 11

Liquid Foundation

TABLE 8

| Phase | Component | wt % |
|---|---|---|
| A1 | PEG-10 dimethicone | 2.0 |
| | BIS-PEG/PPG-14/14 dimethicone-dyclopentasiloxane | 1.0 |
| | Cyclopentasiloxane | 14.5 |
| | Dimethicone | 1.0 |
| | Ethylhexylmethoxycinnamate | 2.5 |
| | Tribehenin | 1.0 |
| | Dimethicone-dimethicone crosspolymer | 8.3 |
| A2 | Composite pigment according to Example 1 | 13.0 |
| | Talc | 1.0 |
| B | Water | 46.0 |
| | Magnesium sulfate | 0.7 |
| | Methylparaben | 0.25 |
| | Phenoxyethanol | 0.5 |
| | Glycerin | 2.75 |
| | Butyleneglycol | 3.5 |
| | Maltitol-sorbitol | 1.0 |
| C | Ethanol | 1.0 |
| Total | | 100 |

Example 12

Skin Care Aerosol Foam

TABLE 9

| Ingredients | Wt % |
|---|---|
| TITANIUM DIOXIDE (and) SILICA (and) ALUMINUM HYDROXIDE (and) ALGINIC ACID | 5 |
| TALC | 5 |
| COMPOSITE PIGMENT ACCORDING TO EXAMPLE 1 | 3 |
| SILICA (and) METHICONE | 1.9 |
| MICA (and) TITANIUM DIOXIDE | 1.425 |
| IRON OXIDES (and) ISOPROPYL TITANIUM TRIISOSTEARATE | 0.209 |
| CALCIUM CARBONATE | 1.9 |
| ETHYLHEXYL METHOXYCINNAMATE | 7.125 |
| OCTOCRYLENE | 2.85 |
| ETHYLHEXYL SALICYLATE | 4.7025 |
| SEA WATER | 7.1725 |
| DIPOTASSIUM GLYCYRRHIZATE | 0.19 |
| SODIUM HYALURONATE | 0.0095 |

TABLE 9-continued

| Ingredients | Wt % |
|---|---|
| BETAINE | 0.475 |
| PEG/PPG/POLYBUTYLENE GLYCOL-8/5/3 GLYCERIN | 2.85 |
| ETHYLHEXYLGLYCERIN | 0.285 |
| CAPRYLYL GLYCOL | 0.475 |
| BUTYLENE GLYCOL | 1.9 |
| ALCOHOL | 0.665 |
| PEG-12 DIMETHICONE | 0.95 |
| PHENOXYETHANOL | 0.3325 |
| TOCOPHERYL ACETATE | 0.0095 |
| FRAGRANCE | 0.0475 |
| ETHANE | 0.005 |
| PROPANE | 1.16 |
| ISOBUTANE | 1.12 |
| BUTANE | 2.67 |
| PENTANE | 0.045 |
| WATER | qsp 100 |
| Total | 100 |

The invention claimed is:

1. A composite pigment comprising: at least one small hollow core particle of spherical shape with a mean particle size ranging from 100 nm to 600 nm, wherein the surface of the at least one small hollow core particle is at least in part covered with at least one coating layer comprising a first metal oxide; and wherein the at least one small hollow core particle comprises at least one copolystyrene; and at least one large solid core particle with a mean particle size of greater than or equal to 2 μm, wherein the surface of the at least one large solid core particle is at least in part covered with at least one coating layer comprising a second metal oxide and/or at least one coloring pigment, and wherein the at least one large solid core particle comprises at least one poly(meth)acrylate, wherein the weight ratio of the total amount of the at least one small hollow core particle to the total amount of the at least one large solid core particle ranges from 70:30 to 80:20.

2. The composite pigment according to claim 1, wherein the at least one coating layer on the small hollow core particle includes at least one coloring pigment.

3. The composite pigment of claim 1, wherein the first metal oxide is titanium oxide.

4. The composite pigment of claim 1, wherein the first metal oxide has a mean particle size ranging from 1 nm to 50 nm.

5. The composite pigment of claim 1, wherein the first metal oxide has at least one coating.

6. The composite pigment of claim 5, wherein the at least one coating of the first metal oxide comprises at least one compound chosen from alumina, silica, aluminum hydroxide, silicones, silanes, fatty acids or salts thereof, fatty alcohols, lecithin, amino acids, polysaccharides, proteins, alkanolamines, waxes, (meth)acrylic polymers, organic UV filters, (per)fluoro compounds, and combinations thereof.

7. The composite pigment of claim 1, wherein the at least one coating layer on the at least one small hollow core particle has a thickness ranging from 1 nm to 50 nm.

8. The composite pigment of claim 2, wherein the at least one coloring pigment is chosen from titanium dioxide, zirconium oxide, cerium oxide, zinc oxide, iron oxide, chromium oxide, manganese violet, ultramarine blue, chromium hydrate, ferric blue, aluminum powder, copper powder, silver powder, gold powder, barium sulfate, carbon black, pigments of D&C type, lakes, pearlescent pigments, silica, and mixtures thereof.

9. The composite pigment of claim 1, wherein the at least one small hollow core particle further comprises at least one inorganic material.

10. The composite pigment of claim 9, wherein the at least one inorganic material is chosen from mica, synthetic mica, talc, sericite, boron nitride, glass flake, calcium carbonate, barium sulfate, titanium oxide, hydroxyapatite, silica, silicate, zinc oxide, magnesium sulfate, magnesium carbonate, magnesium trisilicate, aluminum oxide, aluminum silicate, calcium silicate, calcium phosphate, magnesium oxide, bismuth oxychloride, kaolin, hydrotalcite, mineral clay, synthetic clay, iron oxide, and mixtures thereof.

11. The composite pigment of claim 1, wherein the weight ratio of the at least one small hollow core particle to the first metal oxide ranges from about 10:90 to 90:10.

12. The composite pigment of claim 1, wherein the at least one large solid core particle further comprises at least one inorganic material.

13. The composite pigment of claim 12, wherein the at least one inorganic material is chosen from mica, synthetic mica, talc, sericite, boron nitride, glass flake, calcium carbonate, barium sulfate, titanium oxide, hydroxyapatite, silica, silicate, zinc oxide, magnesium sulfate, magnesium carbonate, magnesium trisilicate, aluminum oxide, aluminum silicate, calcium silicate, calcium phosphate, magnesium oxide, bismuth oxychloride, kaolin, hydrotalcite, mineral clay, synthetic clay, iron oxide, and mixtures thereof.

14. A cosmetic composition comprising, in a cosmetically suitable medium: a composite pigment comprising: at least one small hollow core particle of spherical shape with a mean particle size ranging from 100 nm to 600 nm; wherein the surface of the at least one small hollow core particle is at least in part covered with at least one coating layer comprising a first metal oxide; and wherein the at least one small hollow core particle comprises at least one copolystyrene; and at least one large solid core particle with a mean particle size of greater than or equal to 2 μm, wherein the surface of the at least one large solid core particle is at least in part covered with at least one coating layer comprising a second metal oxide and/or at least one coloring pigment, and wherein the at least one large solid core particle comprises at least one poly(meth)acrylate; wherein the weight ratio of the total amount of the at least one small hollow core particle to the total amount of the at least one large solid core particle ranges from 70:30 to 80:20.

15. A cosmetic agent for the photoprotection against UV radiation, comprising: at least one composite pigment comprising: at least one small hollow core particle of spherical shape with a mean particle size ranging from 100 nm to 600 nm; wherein the surface of the at least one small hollow core particle is at least in part covered with at least one coating layer comprising a first metal oxide; and wherein the at least one small hollow core particle comprises at least one copolystyrene; and at least one large solid core particle with a mean particle size of greater than or equal to 2 μm, wherein the surface of the at least one large solid core particle is at least in part covered with at least one coating layer comprising a second metal oxide and/or at least one coloring pigment, and wherein the at least one large solid core particle comprises at least one poly(meth)acrylate; wherein the weight ratio of the total amount of the at least one small hollow core particle to the total amount of the at least one large solid core particle ranges from 70:30 to 80:20.

16. A composite pigment comprising:
at least one small hollow core particle comprising at least one organic polymer, wherein the at least one small hollow core particle has a mean particle size ranging from 100 nm to 600 nm and comprises at least one copolystyrene, and wherein the surface of the at least one small hollow core particle is at least partially covered with at least one coating layer comprising at least one inorganic solid UV filter; and at least one large solid core particle, wherein the at least one large solid core particle has a mean particle size of greater than or equal to 2 μm and comprises at least one poly(meth)acrylate, and wherein the surface of the at least one large solid core particle is at least partially covered with at least one coating layer comprising:

at least one inorganic solid UV filter comprising titanium oxide; and/or at least one coloring pigment;

wherein the composite pigment has a weight ratio of the total amount of small hollow core particles to the total amount of large solid core particles to the total amount of inorganic solid UV filters ranging from 20:50:30 to 50:20:30.

17. A cosmetic composition comprising:

at least one composite pigment according to claim 16; and at least one additional component chosen from fillers, oils, water, or mixtures thereof;

wherein the composition comprises a total amount of composite pigment ranging from 0.01% to 99% by weight, relative to the total weight of the composition.

\* \* \* \* \*